United States Patent
Huang et al.

(10) Patent No.: US 9,427,424 B2
(45) Date of Patent: Aug. 30, 2016

(54) USE OF HISTONE DEACETYLASE INHIBITORS IN CHANGING MRJP3 PROTEIN IN ROYAL JELLY

(71) Applicant: NATUREWISE BIOTECH & MEDICALS CORPORATION, Taipei (TW)

(72) Inventors: Chung-Yang Huang, Taipei (TW); Chia-Nan Chen, Taipei (TW); Wei-Jung Chen, Taipei (TW); Wei-Jan Huang, Taipei (TW); Li-Ling Chi, Taipei (TW)

(73) Assignee: Naturewise Biotech & Medicals Corporation, Taipei (TW)

( * ) Notice: Subject to any disclaimer, the term of this patent is extended or adjusted under 35 U.S.C. 154(b) by 22 days.

(21) Appl. No.: 14/299,568

(22) Filed: Jun. 9, 2014

(65) Prior Publication Data

US 2014/0288166 A1    Sep. 25, 2014

Related U.S. Application Data

(62) Division of application No. 12/507,545, filed on Jul. 22, 2009, now Pat. No. 8,784,873.

(51) Int. Cl.
*A61K 31/353* (2006.01)
*A01K 53/00* (2006.01)
*A61K 31/185* (2006.01)
*A61K 35/644* (2015.01)

(52) U.S. Cl.
CPC ............. *A61K 31/353* (2013.01); *A01K 53/00* (2013.01); *A61K 31/185* (2013.01); *A61K 35/644* (2013.01); *Y02P 20/582* (2015.11)

(58) Field of Classification Search
CPC ................................................... A61K 31/353
See application file for complete search history.

*Primary Examiner* — Andrew D Kosar
*Assistant Examiner* — John S Kenyon
(74) *Attorney, Agent, or Firm* — WPAT, P.C., Intellectual Property Attorneys; Anthony King

(57) ABSTRACT

The invention provides a method of changing a ratio of 68 to 64 kDa protein of MRJP3 in a royal jelly, a method of producing a royal jelly comprising MRJP3 having a changed ratio of 68 to 64 kDa protein relative to a control royal jelly and the royal jelly produced thereform. Also provided is a method of promoting the growth of the larva of a queen bee comprising feeding the larva of the queen bee a royal jelly of the invention. Further provided is a method of producing bee larva, pupa and queen bees with sizes larger than normal.

12 Claims, 11 Drawing Sheets

Figure 1

USE OF HISTONE DEACETYLASE INHIBITORS IN CHANGING MRJP3 PROTEIN IN ROYAL JELLY

FIELD OF THE INVENTION

The invention relates to a method of promoting the growth of bee larvae, pupas and queen bees by feeding the young worker (nursing) bees a histone deacetylase inhibitor (HDACi) or a mixture or recipe containing HDAC inhibitor (s). In particular, the royal jelly secreted by the young worker bees fed on the HDACi may have a changed ratio of 68 to 64 kDa protein of MRJP3.

BACKGROUND OF THE INVENTION

Honeybees are one of the most beneficial organisms in contemporary agriculture and they provide various products such as royal jelly, honey, propolis, and pollens, which serve as nutrition sources for human beings (Hellner M et al., 2008). Therefore, there have been great interests in the growth, evolution, and development of honey bees.

Honeybees live in matrilineal societies, and a bee colony is led by the queen bee. In a bee colony, worker bees and the queen bee are developed from fertilized eggs while drones are developed from unfertilized eggs (Winston M. L., 1987). The queen lays eggs singly in cells of the comb. Larvae hatch from eggs in three to four days. They are then fed by young worker bees and develop through several stages in the cells. Cells are capped by worker bees when the larva pupates. Queens emerge from their cells in 16 days, workers in 21 days and drones in 24 days. Queens are bigger in body size, and their lifespan is normally 10 to 15 times that of worker bees. Whether a fertilized egg develops into a worker bee or a queen is regulated by the bee colony. In principle, only one queen is present in a bee colony. Besides, a queen bee is fed differently from other bees in the same colony. The queen bee is fed royal jelly throughout its life, and worker bees are only fed royal jelly at the beginning of their development. While some researchers believe that worker bees are also fed royal jelly throughout their developmental stage, the royal jelly fed to worker bees may have different chemical constituents from that fed to the queen. In any case, royal jelly serves as the most important substance in maintenance of a bee colony (Robinson G. E. et al., 1987).

Royal jelly is the most important food and nutrition source for larvae of the queen bee and the queen. It is secreted by the hypopharyngeal and mandibular glands of young worker bees and the constituents of royal jelly may change at the different developmental stages of the larvae. In general, such change is considered to be reflected in the sugars rather than protein components of royal jelly (Peiren N. et al., 2005).

It is known that royal jelly comprises many substances capable of improving human health and has various pharmacological properties (Takaki-Doi S. et al., 2009; Mannoor M. K. et al., 2009; and Gasic S. et al., 2007). Therefore, royal jelly has been widely used in health food intended to promote human health. Recently, researches demonstrated that royal jelly is capable of promoting immune regulations (Vuecvic D. et al., 2007), exhibiting anti-bacterial functions (Boukraa L., 2008), nourishing cerebral nerves (Hashimoto M. et al., 2005), exhibiting anti-cancer and antioxidant activities (Guo H. et al., 2008). It has been found that royal jelly, which is opal thick liquid, is around 60-70% water, 12-15% proteins, 10-12% sugars, 3-5% lipids, and many trace elements and minerals (Scarselli R. et al., 2005). Among the protein components, around 89-90% are water-soluble proteins, and the rest are water-insoluble proteins. In other words, most of the proteins contained in royal jelly are water-soluble.

The MRJP (major royal jelly proteins; MRJP) family (MRJP 1-9) is the major component among these water-soluble proteins (Schmitzová J. et al, 1998). Although these MRJP proteins have been analyzed for their amino acid sequences, their functions are still unclear.

MRJP1 was identified in the brain of bees, and is assumed to be responsible for bees' behaviors. It accounts for 44% of the water-soluble proteins in royal jelly, and is the most abundant isoform among the MRJP family proteins (Malecová B. et al., 2003). To date, MRJP3 has received most attention, and it is considered that this protein plays a role in immune regulation (Kohno K. et al., 2004). It has also been found that MRJP3 accounts for 12% of total water-soluble proteins in royal jelly, and is the second most abundant isoform among all MRJP proteins (MRJPs 1-9). MRJP3 is distinct due to its antiallergic and anti-inflammatory activities. The 60-70 kDa proteins are variants of MRJP3 protein which is the product of the highly polymorphic MRJP gene (Stefan Albert et al., 1999).

MRJPs provide abundant essential amino acids and other nutrient components (Furusawa T et al., 2008). As royal jelly is the only nutrition source for larvae of the queen bee and MRJPs are the most important proteins in royal jelly, there is a need to develop the royal jelly with specific components.

SUMMARY OF THE INVENTION

The invention provides a method of producing a bee larva that is at least one time larger and may be several times larger than normal, a pupa that is at least 50% larger and may be one to several times larger than normal, and a queen bee that is at least 50% larger and may be one time to several times larger than normal.

The invention provides a method of producing bee larvae that are at least one time weight than control larvae comprising feeding young worker bees a HDAC inhibitor or a mixture thereof and feeding bee larvae royal jelly secreted by these young worker bees, while the bee larvae of the control receive the royal jelly produced by young worker bees not fed with a HDAC inhibitor or a mixture thereof.

The invention provides a method of producing a pupa that is at least 50% weight than a control pupa or a queen bee that is at least 50% weight than a control queen bee, comprising feeding young worker bees a HDAC inhibitor or a mixture thereof, feeding a bee larva royal jelly secreted by these young worker bees and obtaining a pupa or queen bee developed from this bee larva while the control pupa or control queen bee is developed from the bee larva that receives the royal jelly produced by young worker bees not fed on a HDAC inhibitor or a mixture thereof.

The invention further provides a royal jelly, comprising MRJP3 having a changed ratio of 68 to 64 kDa protein relative to a control royal jelly.

The invention further provides a method of regulating epigenetics on the mrjp3 gene in worker bees, comprising feeding worker bees a HDAC inhibitor to regulate the expression of the mrjp3 gene in worker bees.

BRIEF DESCRIPTION OF THE DRAWING

FIG. 1 shows that young worker bees fed on Taiwanese Green Propolis extract secreted special royal jelly which induced rapid growth of the larvae. U-1 and U-2: control group; A-1 and A-2: treated with 1.25 g/kg of Taiwanese Green Propolis extract; B-1 and B-2: treated with 2.50 g/kg of Taiwanese Green Propolis extract; C-1 and C-2: treated with 5.0 g/kg of Taiwanese Green Propolis extract.

DETAILED DESCRIPTION OF THE INVENTION

Figure 2:
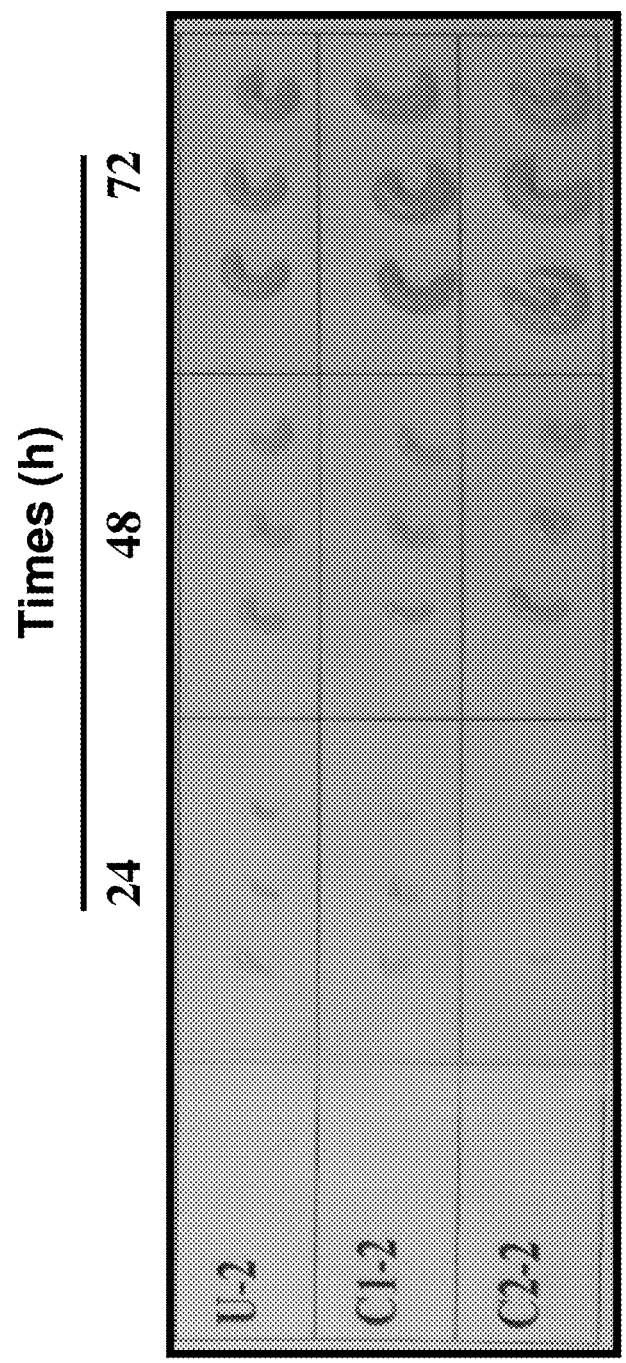
FIG. 2 demonstrates that young worker bees fed on propolin C secreted special royal jelly which induced rapid growth of the larvae. U-2: control group; C1-2: treated with 50 mg/kg of propolin C; C2-2: treated with 100 mg/kg of propolin C.

The invention discovers that worker (nursing) bees fed on a HDAC inhibitor or a mixture thereof can raise the bee larvae at a fast growth rate resulting in large larvae, pupas and queen bee. The bee larvae can be at least one time larger and may be several times larger than normal, the pupas can be at least 50% larger and may be one to several times larger than normal, and the queen bees can be at least 50% larger and may be one time to several times larger than normal.

The invention discovers that a HDAC inhibitor or the mixture thereof can change the ratio of 68 to 64 kDa protein of MRJP3 in royal jelly through epigenetics. Young worker bees fed on HDAC inhibitor or a mixture thereof will produce a specific royal jelly through epigenetics wherein the ratio of 68 to 64 kDa protein is charged. Royal jelly is the main food of larvae of the queen bee and the queen. The invention found that a specific royal jelly will promote the growth of larvae of the queen bee fed thereon and the weight of the larvae and the resulting pupas and queen bees increases significantly.

In one aspect, the invention provides a method of producing bee larvae that are at least one time weight than control larvae comprising feeding young worker bees a HDAC inhibitor or a mixture thereof and feeding bee larvae royal jelly secreted by these young worker bees, while the bee larvae of the control receive the royal jelly produced by young worker bees not fed on a HDAC inhibitor or a mixture thereof. According to an embodiment of the invention, the bee larvae can be fed by worker bees with the royal jelly that they secrete or by human with the royal jelly collected from worker bees. According to an embodiment of the invention, the weight of the larvae feeding on the above-mentioned royal jelly after 72 hrs increases by higher than 1.5 times. Preferably, the weight increases by about 2 to 5 times. More preferably, the weight increases by about 3 to 5 times. According to the invention, the royal jelly mentioned above comprises MRJP3 having a changed ratio of 68 to 64 kDa protein relative to a control royal jelly.

According to the invention, the pupa and queen bee developed from the bee larva of the invention will have higher weight than the control pupa and queen bee, respectively. Accordingly, the invention provides a method of producing a pupa that is at least 50% weight than a control pupa or queen bee that is at least 50% weight than a control queen bee, comprising feeding young worker bees a HDAC inhibitor or a mixture thereof, feeding a bee larva with royal jelly secreted by these young worker bees and obtaining a pupa or queen bee developed from this bee larva while the control pupa or control queen bee is developed from the bee larva that receives the royal jelly produced by young worker bees not fed on a HDAC inhibitor or a mixture thereof. According to an embodiment of the invention, the bee larvae can be fed by worker bees with the royal jelly that they secrete or by human with the royal jelly collected from worker bees.

In one aspect, the invention provides a method of changing a ratio of 68 to 64 kDa protein of MRJP3 in a royal jelly, comprising feeding young worker bees a HDAC inhibitor or a mixture thereof to produce, relative to a control royal jelly, a royal jelly having a changed ratio of 68 to 64 kDa protein of MRJP3.

In another aspect, the invention provides a method of producing a royal jelly comprising MRJP3 having a changed ratio of 68 to 64 kDa protein relative to a control royal jelly, comprising feeding young worker bees a HDAC inhibitor or a mixture thereof and collecting the royal jelly produced by the young worker bees.

In another aspect, the invention further provides a royal jelly, comprising MRJP3 having a changed ratio of 68 to 64 kDa protein relative to a control royal jelly.

According to the invention, the ratio of 68 to 64 kDa protein of MRJP3 can increase by about 1.5 to 12 times, 1.5 to 5 times, 2-6 times, 2-10 times, 4-12 times or 2-4 times relative to a control. More preferably, the ratio of 68 to 64 kDa protein of MRJP3 can increase by about 1.5 to about 5 times or 2 to 10 times relative to a control. More preferably, the ratio of 68 to 64 kDa protein of MRJP3 can increase by about 2 to 4 times or about 4 to 10 times relative to a control.

In another further aspect, the invention provides a method of regulating epigenetics on the MRJP3 gene in worker bees, comprising feeding worker bees a HDAC inhibitor or a mixture thereof to regulate the expression of the MRJP3 gene in worker bees. According to the invention, the epigenetics may be inhibition of DNA methylation or HDAC. DNA methylation is an epigenetic change that is a heritable change in gene expression without a change in the DNA sequence. DNA methylation is a covalent modification that triggers heritable gene silencing. DNA methylation triggers silencing in one of two ways. First, methylation can directly interfere with transcription factor binding to recognition sites on DNA. Second, methyl-CpG binding domain proteins (MBPs) can reinforce silencing by recruiting co-repressor complexes that harbor histone deacetylases or histone methyltransferases (Julie C. Kiefer, 2007). As the HDAC inhibitor changes the expression of the 68 and 64 kDa proteins of MRJP3 in young worker bees, it is suggested that the HDAC inhibitor can regulate Histones hyperacetylation and influence the polymophlic mrjp3 gene splicing and translation in young work bees.

In the context of the present specification, the term "alkyl" means straight or branched hydrocarbon chains. The alkyl is preferably $C_{1-10}$ alkyl. Preferably, the carbon number of alkyl is selected from the group consisting of 1 to 8; more preferably, it is $C_{1-6}$ alkyl or $C_{1-4}$ alkyl. Examples of alkyl groups include methyl (—$CH_3$), ethyl (—$CH_2CH_3$), propyl (—$CH_2CH_2CH_3$), isopropyl ($(CH_3)_2CH$) and butyl (—$C_4H_9$).

In the context of the present specification, the term "alkenyl" means both straight and branched chain unsaturated hydrocarbon groups, wherein the unsaturation is present only as double bonds. According to the invention, the alkenyl includes one or more double bonds. The alkenyl is preferably $C_{2-16}$ alkenyl. More preferably, the carbon number of alkenyl is selected from the group consisting of 2 to 12. Examples of alkenyl groups include ethenyl (—CH=$CH_2$), propenyl (—CH=$CHCH_3$ or —$CH_2CH$=$CH_2$), butenyl (—$CH_2CH$=$CHCH_3$ or —CH=$CHCH_2CH_3$ or —$CH_2CH_2CH$=$CH_2$), —$CH_2CH$=$C(CH_3)CH_3$, —$CH_2$—CH=CH—$CH_2$—$CH_2$—CH=CH—$CH_3$ and —$CH_2$—CH=$C(CH_3)$—$CH_2$—$CH_2$—CH=$C(CH_3)$—$CH_3$.

In the context of the present specification, the term "cycloalkyl" means an aliphatic ring (saturated carbocyclic ring). Preferably, the carbon number of cycloalkyl is selected from the group consisting of 3 to 8. More preferably, the carbon number of cycloalkyl is selected from the group consisting of 5 to 6. Examples of cycloalkyl groups include cyclopropyl, cyclobutyl, cyclopentyl and cyclohexyl.

In the context of the present specification, the term "unsaturated carbocycle" includes a cyclic substituent consisting of carbon atom and hydrogen atom, and the cyclic part is unsaturated cycle, for example, aryl or cycloalkenyl or the like. The term "cycloalkenyl" includes alkenyl which is the cycloalkyl having one or more double bond, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl, and 3-cyclopenten-1-yl), cyclohexenyl (e.g., 1-cyclohexen-1-yl, 2-cyclohexen-1-yl, and 3-cyclohexen-1-yl), cycloheptenyl (e.g., 1-cycloheptenyl), cyclooctenyl (e.g., 1-cyclooctenyl) or the like. Especially, preferred is 1-cyclohexen-1-yl, 2-cyclohexen-1-yl, or 3-cyclohexen-1-yl. The term "aryl" includes single and fused rings wherein at least one ring is aromatic, for example, phenyl, naphthyl and tetrahydronaphthalenyl.

In the context of the present specification, the phrase "5-membered or 6-membered heterocycle" refers to a cyclic ring of five or six atoms, wherein at least one atom of the ring is a heteroatom. The 5-membered or 6-membered heterocycle can be aromatic or non-aromatic which is saturated or unsaturated. Preferably, the heteroatom is selected from N, O and S. Examples of heterocycle includes, but not limited to, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl) tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl) pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like.

In the context of the present specification, the term "halogen" means fluorine, chlorine, bromine and iodine.

In the context of the present specification, the term "pharmaceutically acceptable salt" includes those formed with both organic and inorganic acids and bases. Pharmaceutically acceptable acid addition salts include those formed from mineral acids such as: hydrochloric, hydrobromic, sulphuric, and phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines.

In the context of the present specification, the term "prodrug" means a compound which is converted within the body, e.g., by hydrolysis in the blood, into its active form that has medical effects.

In the context of the present specification, the term "solvate" means a complex comprising the compound of the invention and a solvent in which they are reacted or from which they are precipitated or crystallized.

In the context of the present specification, the term "stereoisomers" are isomeric molecules whose atomic connectivity is the same but whose atomic arrangement in space is different.

In the context of the present specification, the term "enantiomers" are stereoisomers that are nonsuperimposable complete mirror images of each other, much as one's left and right hands are "the same" but opposite.

In the context of the present specification, the term "worker bee" is any female eusocial bee that lacks the full reproductive capacity of the colony's queen bee; under most circumstances, this is correlated to an increase in certain non-reproductive activities relative to a queen, as well. Bee eggs are laid singly in a cell in a wax honeycomb, produced and shaped by the worker bees. Larvae are initially fed with royal jelly produced by worker bees, later switching to honey and pollen. The exception is a larva fed solely on royal jelly, which will develop into a queen bee. The larva undergoes several molting before spinning a cocoon within the cell, and pupating. Drones hatch from unfertilized eggs, females (queens and worker bees) hatch from fertilized eggs. The queen actually can choose to fertilize the egg she is laying, usually depending on what cell she is laying in. Young worker bees clean the hive and feed the larvae. When their royal jelly producing glands begin to atrophy, they begin building comb cells. They progress to other within-colony tasks as they become older, such as receiving nectar and pollen from foragers, and guarding the hive. Later still, a worker takes her first orientation flights and finally leaves the hive and typically spends the remainder of her life as a forager.

In the context of the present specification, the term "royal jelly" is a honey bee secretion that is used in the nutrition of the larvae. It is secreted from the hypopharyngeal glands in the heads of young workers and used (among other substances) to feed the larvae in the colony.

According to the invention, HDAC is an enzyme that influences transcription by selectively deacetylating the ε-amino groups of lysine located near the amino termini of core histone proteins. HDAC inhibitors are emerging as an exciting new class of potential anticancer agents for the treatment of solid and hematological malignancies. The invention unexpectedly found that a HDAC inhibitor affects the expression of 68 and 64 kDa proteins of MRJP3 in a royal jelly produced by young worker bees. According to invention, the HDAC inhibitor includes but not limited to four classes of HDAC inhibitors, short-chain fatty acids, hydroxamic acids, benzamides and cyclic peptides, reported in Medicinal Research Reviews, Vol. 26, No. 4, pp. 397-413, 2006; Hydroxamic acid-based hybrid polar compounds (HPCs) mentioned in Journal of the National Cancer Institute, Vol. 92, No. 15, Aug. 2, 2000, pp. 1210-1216; benzamide derivatives in U.S. Pat. No. 6,174,905, EP 0847992, JP 258863/96, and Japanese Application No. 10138957; the compounds in WO 01/38322; benzamide M344 (Hum Genet, 2006, 120, pp. 101-110); sodium butyrate (Human Molecular Genetics, 2004, Vol. 13, No. 11, pp. 1183-1192); Trichostatin A (Molecular Cancer 2006, 5:8); the compounds having the formula Z-Q-L-M or Z-L-M disclosed in U.S. Pat. No. 7,169,801; a family of Sulphonamide compounds including PXD101 in U.S. Pat. No. 6,888,027; valproic acid and its derivatives covered in European Patent Number EP 1 301 184; N,N'-hexamethylene bisacetamide (HMBA); the compounds related to HMBA mentioned in U.S. Pat. Nos. 6,087,367 and RE38506; the compounds related to HMBA such as suberoylanilide hydroxamide acid (SAHA) disclosed in U.S. Pat. No. 7,399,787; NVP-LAQ824 (a hydroxamic acid derivative) and NVP-LAQ824 (a derivative of 4-aminomethylcinnamic hydroxamic acid) reported in Blood, 1 Oct. 2003, Vol. 102, No. 7, pp. 2615-2622; LBH589 induces growth inhibition and regression in tumor cell lines by triggering apoptosis and LBH589 is now being tested in phase I clinical trials as an anticancer agent (Blood 105(4): 1768-76 Feb. 15, 2005); the compounds mentioned in U.S. patent application Ser. Nos. 11/855,416 and 12/418,373; propolis, propolins and the compounds in U. S. Publication No. 20080242648 including pyroxamide, M-carboxycinnamic acid bishydroxamide (CBHA), trichostatin A (TSA), trichostatin C, salicylihydroxamic acid (SBHA), azelaic bishydroxamic acid (ABHA), azelaic-1-hydroxamate-9-anilide (AAHA), 6-(3-chlorophenylureido) carpoic hydroxamic acid (3C1-UCHA), oxamflatin, A-161906, scriptaid, PXD-101, cyclic hydroxamic acid-containing peptide (CHAP), ITF-2357, MW2796, MW2996, trapoxin A, FR901228 (FK 228 or Depsipeptide), FR225497, apicidin, CHAP, HC-toxin, WF27082, chlamydocin, sodium butyrate, isovalerate, valerate, 4-phenylbutyrate (4-PBA), 4-phenylbutyrate sodium (PBS), arginine butyrate, propionate, butyramide, isobutyramide, phenylacetate, 3-bromopropionate, tributyrin, valproic acid, valproate, CI-994, 3'-amino derivative of MS-27-275, MGCD0103 and Depudecin. All publications cited herein are incorporated by reference.

According to one embodiment of the invention, the HDAC inhibitors used herein are the compounds represented by the following formula (I):

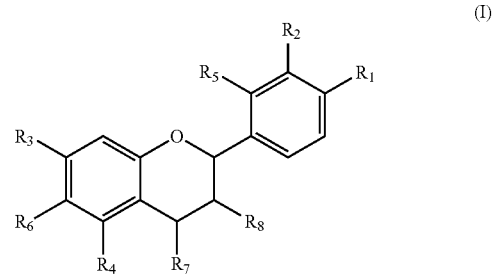

wherein
$R_1$ and $R_2$ are each independently OH, OC(=O)alkyl, O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S; or
$R_1$ and $R_2$ can together form dioxolane;
$R_3$ and $R_4$ are each independently OH, OC(=O)alkyl, O-alkyl, S-alkyl, N-alkyl, O-alkenyl, S-alkenyl, N-alkenyl, O-alkynyl, S-alkynyl, N-alkynyl, O—$C_{3-8}$cycloalkyl, S—$C_{3-8}$cycloalkyl, N—$C_{3-8}$cycloalkyl, O-unsaturated 5- to 10-membered monocyclic or bicyclic ring, S-unsaturated 5- to 10-membered monocyclic or bicyclic ring, N-unsaturated 5- to 10-membered monocyclic or bicyclic ring, alkyl, alkylenyl, alkynyl, $C_{3-8}$cycloalkyl, an unsaturated 5- to 10-membered monocyclic or bicyclic ring or a saturated or unsaturated 5- to 10-membered heterocyclic ring comprising at least one ring heteroatom selected from the group consisting of: N, O and S;

$R_5$ is $C_{4-16}$ alkyl or $C_{4-16}$ alkenyl wherein the alkyl or alkenyl is unsubstituted or substituted with one or more $C_{1-6}$ alkyl, OH, halogen, CN, NO, $N_3$, $NH_2$, CHO, $OR_9$, $SR_9$, $NR_9$, or $COOR_9$;

$R_6$ is $C_{2-12}$ alkyl or $C_{2-12}$ alkenyl wherein the alkyl or alkenyl is unsubstituted or substituted with one or more $C_{1-6}$ alkyl, OH, halogen, CN, NO, $N_3$, $NH_2$, CHO, $OR_9$, $SR_9$, or $NR_9$; or one of $R_5$ and $R_6$ is hydrogen, halogen or OH, while the other is $C_{4-16}$ alkyl or $C_{4-16}$ alkylene unsubstituted or substituted with one or more $C_{1-6}$ alkyl, OH, $NH_2$, halogen, CN, NO or $N_3$;

$R_7$ and $R_8$ are each independently hydrogen, halogen, OH, $NH_2$, COOH, CHO, CN, NO, $C_{1-6}$ alkyl unsubstituted or substituted with OH, $NH_2$, COOH, halogen, CN, NO or CHO, =O, O-alkyl, S-alkyl, N-alkyl, O-alkenyl, S-alkenyl, N-alkenyl, O-alkynyl, S-alkynyl or N-alkynyl, or $R_7$ and $R_8$ may together form a double bond, a $C_{3-6}$ cycloalkyl, or a 5- to 10-membered heterocyclic ring comprising at least a heteroatom selected from the group consisting of N, O and S;

$R_9$ is phenyl, $C(=O)R^{10}$, $C(=O)OR^{10}$ or benzyl; and $R^{10}$ is OH, NHOH, $NH_2$, $C_{1-6}$ alkyl, phenyl or benzyl;

and pharmaceutically acceptable salts, stereoisomers, enantiomers, prodrugs and solvates thereof. Preferably, the compounds of formula (I) are those wherein $R_1$ and $R_2$ are each independently OH, OC1-6alkyl, OC(=O)C1-6alkyl, O-phenyl or O-benzyl or $R_1$ and $R_2$ together form dioxalene; $R_3$ and $R_4$ are each independently OH, $OC_{1-6}$ alkyl, OC(=O) $C_{1-6}$ alkyl, O-phenyl or O-benzyl;

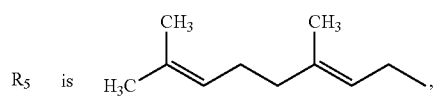

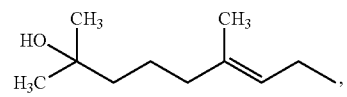

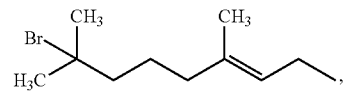

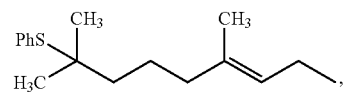

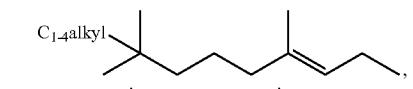

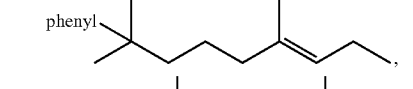

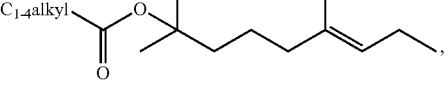

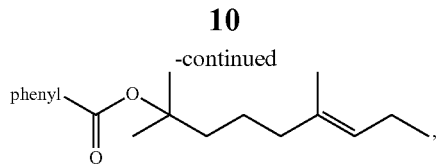

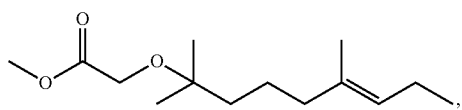

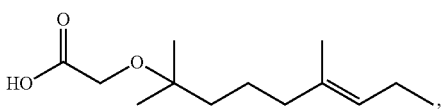

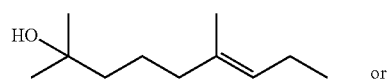

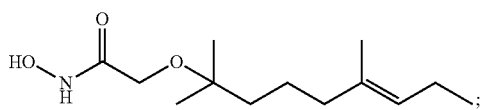

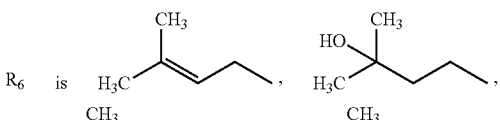

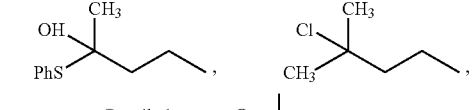

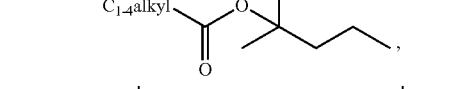

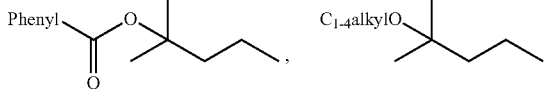

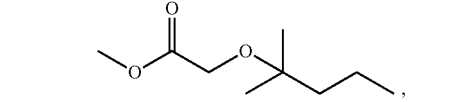

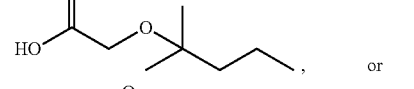

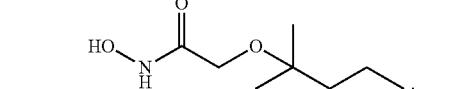

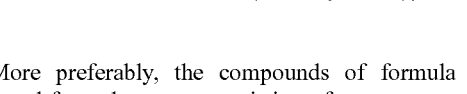

More preferably, the compounds of formula (I) are selected from the group consisting of:

11
12
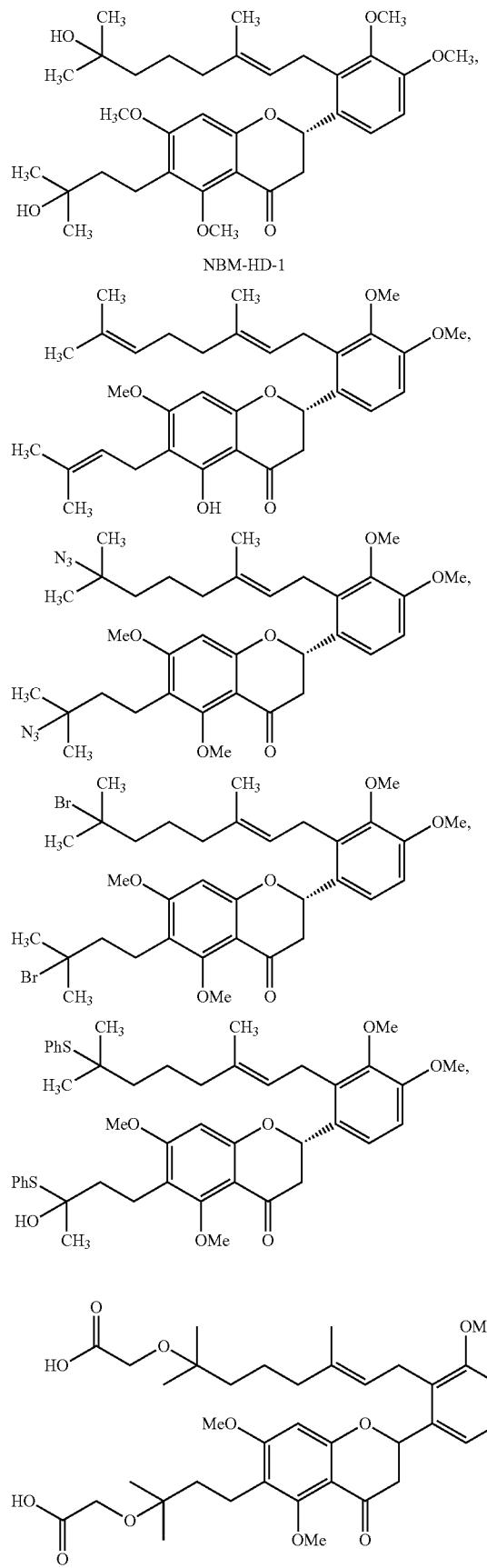
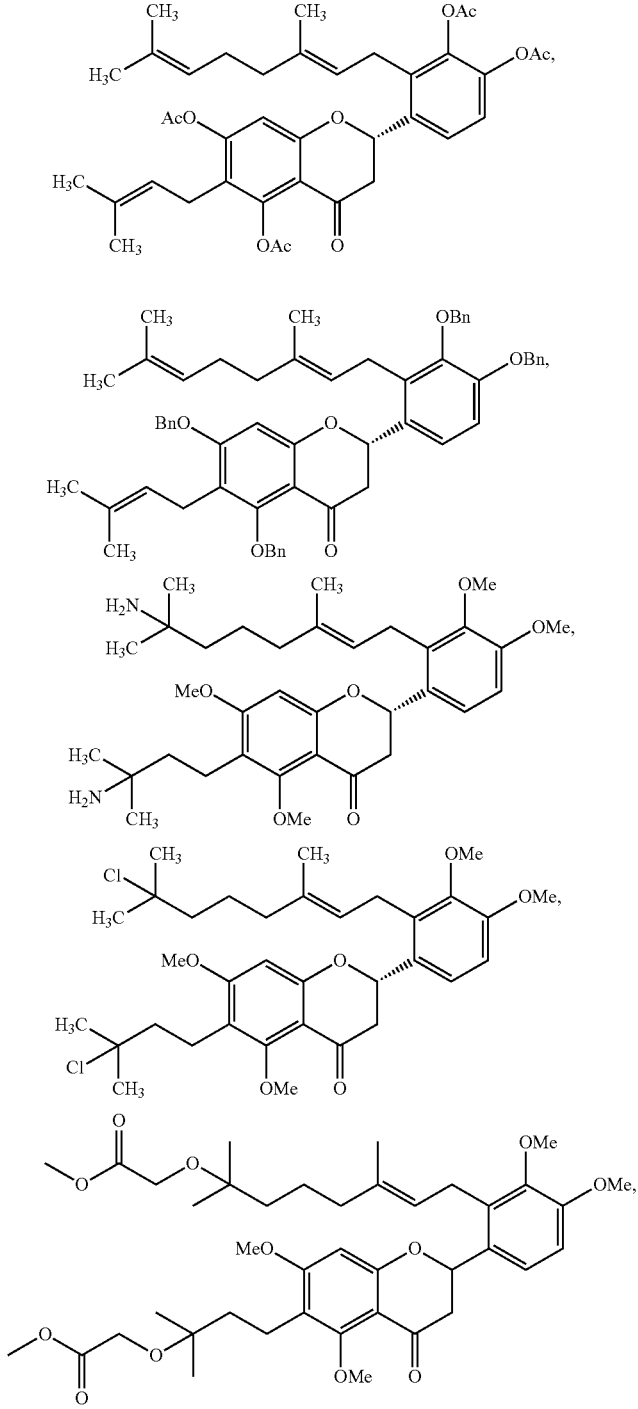

-continued
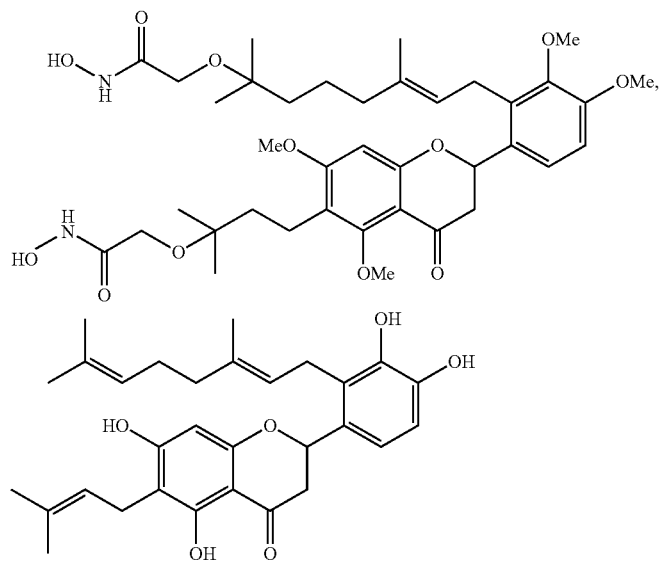
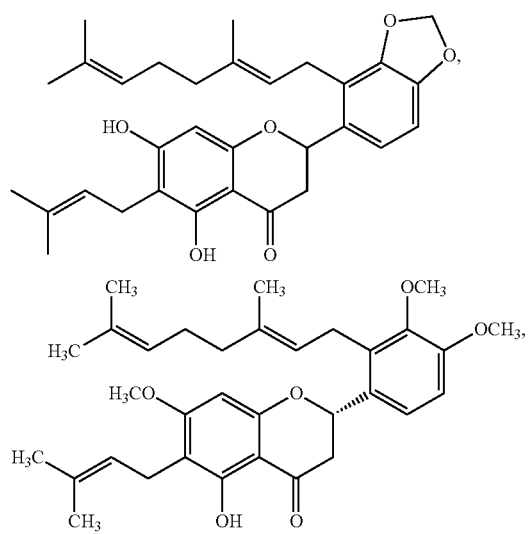
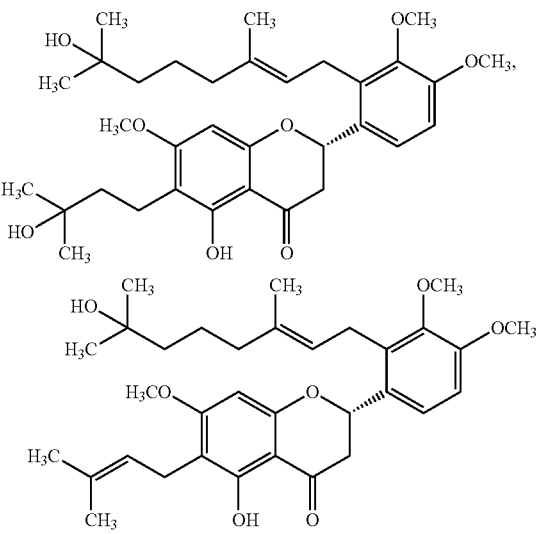
Proplin A
Propolin G
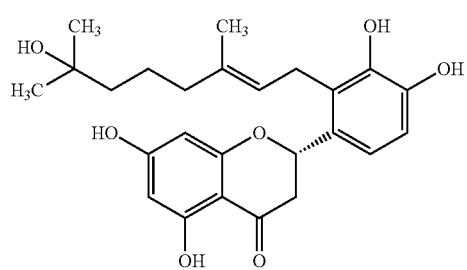
and

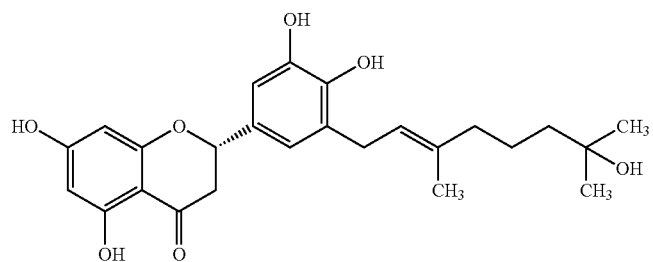
Propolin B
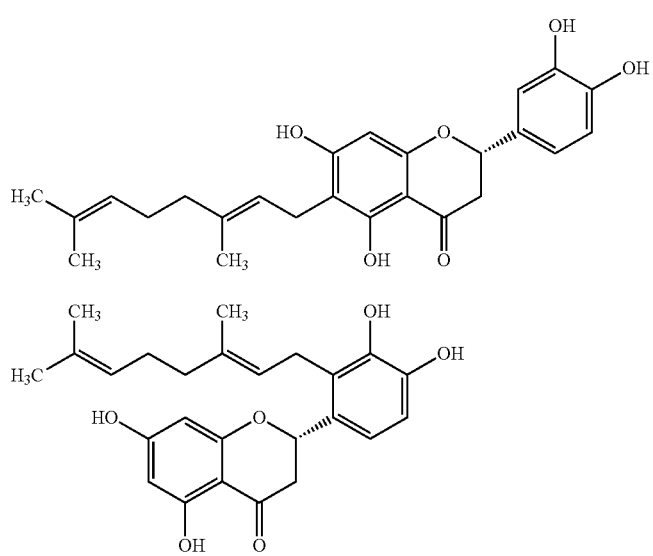
Propolin C
Propolin D
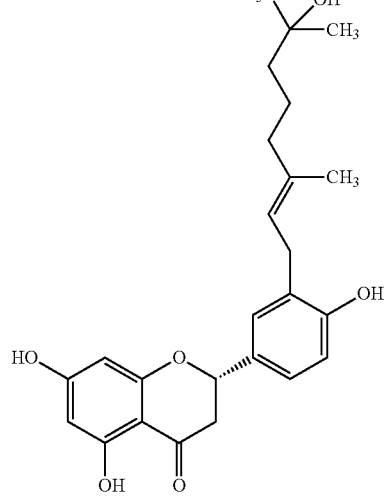
Propolin E
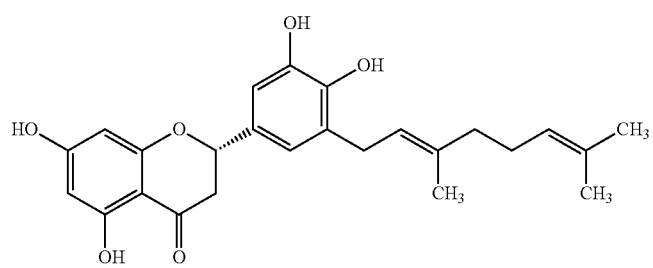
Propolin F -continued
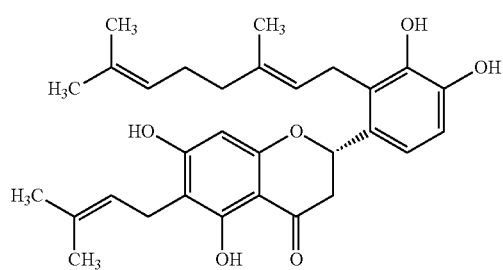
Propolin G
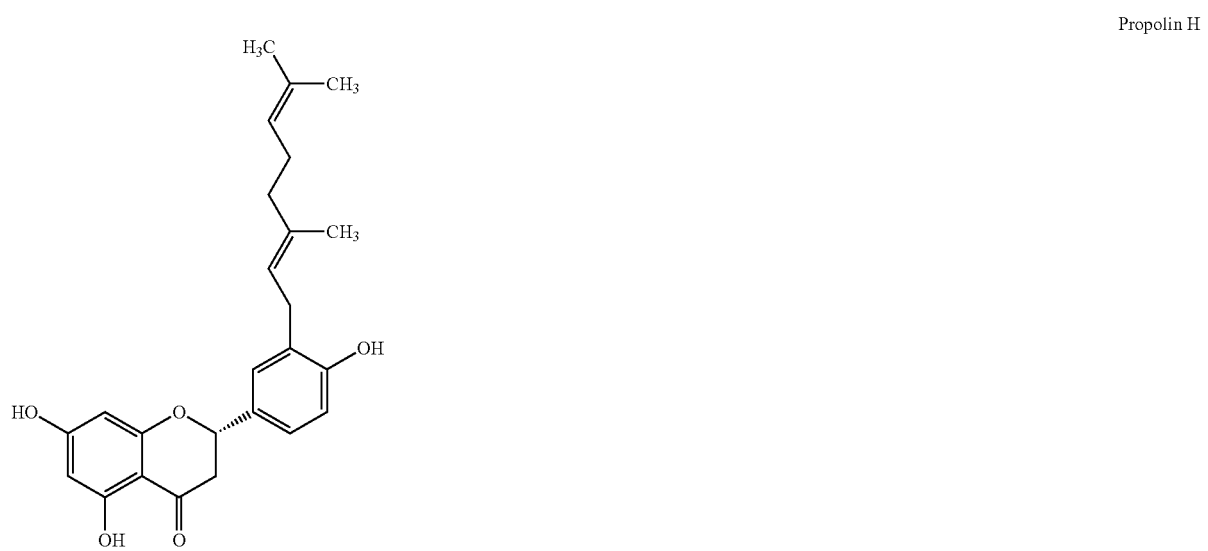
Propolin H
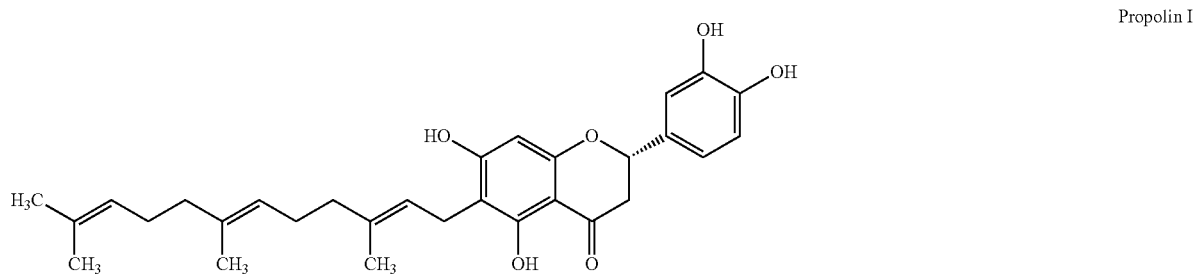
Propolin I
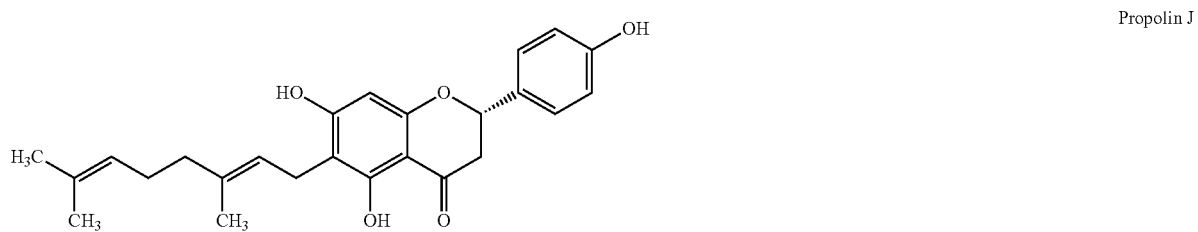
Propolin J According to another embodiment of the invention, the HDAC inhibitors used herein are the compounds represented by the following formula (II):

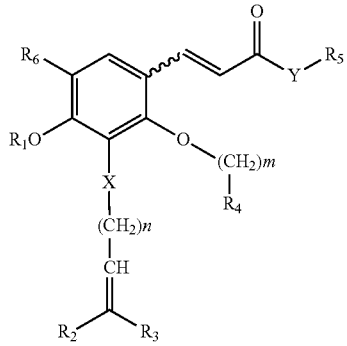

(II)

wherein $R_1$ is hydrogen, alkyl, alkenyl, $C_{5-6}$ cycloalkyl, 5-membered or 6-membered unsaturated carbocycle or 5-membered or 6-membered heterocycle;

X is C, O, N or S;

Y is O, NH or O—$C_{1-4}$alkyl;

n is an integer of 0 to 10;

m is an integer of 0 to 5;

$R_2$ and $R_3$ is independently $C_{1-6}$ alkyl;

$R_4$ is $C_{5-6}$ cycloalkyl or 5-membered or 6-membered unsaturated carbocycle or heterocycle which may be substituted with halogen, $CF_3$, $OR_7$ or $NR_7R_8$, wherein $R_7$ and $R_8$ are independently hydrogen or $C_{1-6}$ alkyl;

$R_5$ is OH, $NH_2$ or $C_{5-6}$ cycloalkyl, 5-membered or 6-membered unsaturated carbocycle or heterocycle wherein the cycloalkyl, carbocycle and heterocycle may be optionally substituted with halogen, $NH_2$, $NO_2$, $C_{1-6}$ alkoxy, $C_{1-6}$ alkylthio, $OR_7$, $NR_7R_8$ or $CF_3$; and $R_6$ is H, $C_{1-10}$alkyl which may be substituted by hydroxy or $C_{2-10}$alkenyl, or together with $R_1$ being —$C_2H_2$—;

and pharmaceutically acceptable salts, stereoisomers, enantiomers, prodrugs and solvates thereof.

Preferably, the compounds of formula (II) are those wherein $R_1$, $R_2$ and $R_3$ are independently $C_{1-4}$ alkyl; $R_4$ is phenyl or phenyl substituted with halogen, $CF_3$, $OC_{1-4}$ alkyl, $R_5$ is OH, phenyl or phenyl substituted with $NH_2$ and $R_6$ is hydrogen;

More preferably, the compounds of formula (II) are selected from the group consisting of:

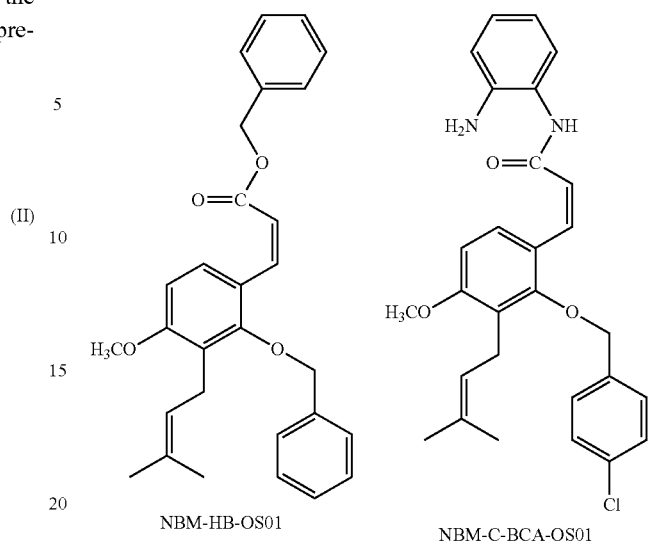

NBM-HB-OS01

NBM-C-BCA-OS01

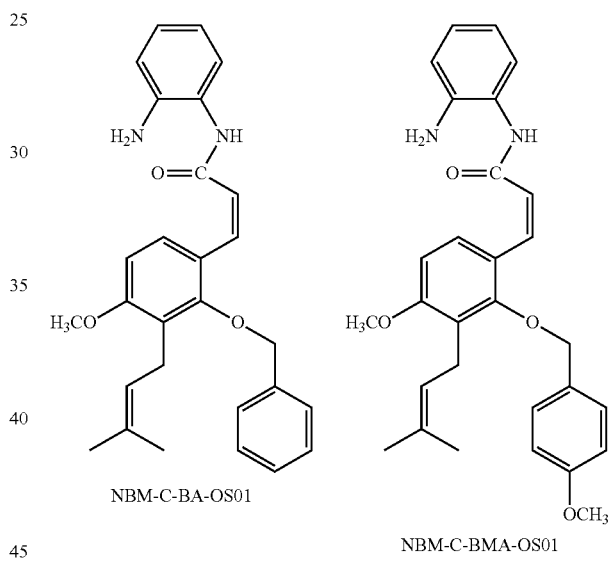

NBM-C-BA-OS01

NBM-C-BMA-OS01

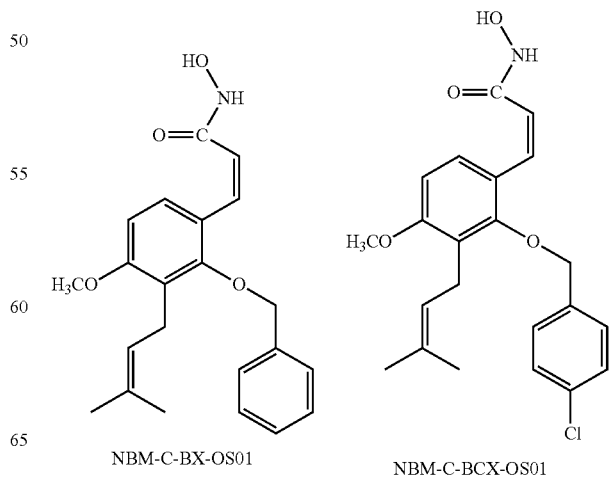

NBM-C-BX-OS01

NBM-C-BCX-OS01

-continued
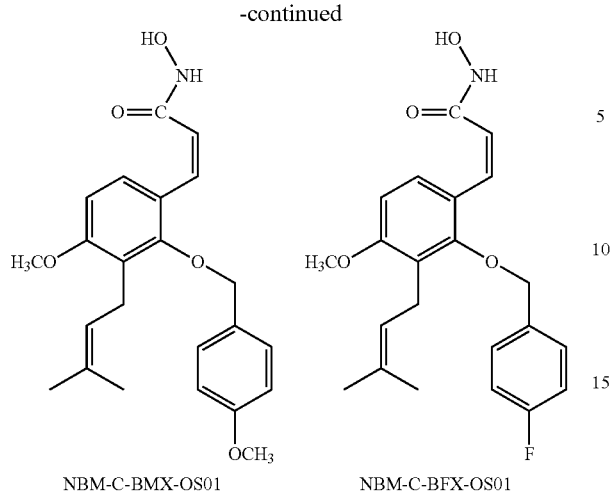
NBM-C-BMX-OS01
NBM-C-BFX-OS01
NBM-C-BBX-OS01
NBM-T-BX-OS01
NBM-T-BA-OS01
-continued
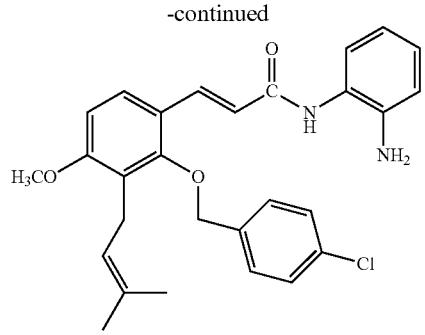
NBM-T-BCA-OS01
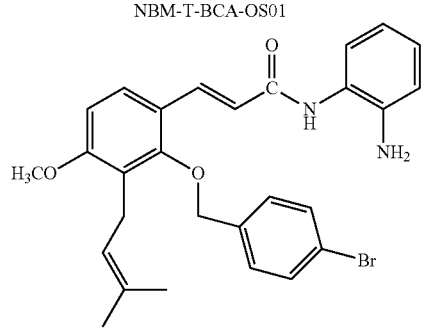
NBM-T-BBA-OS01
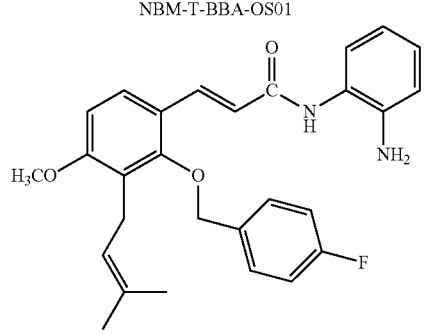
NBM-T-BFA-OS01
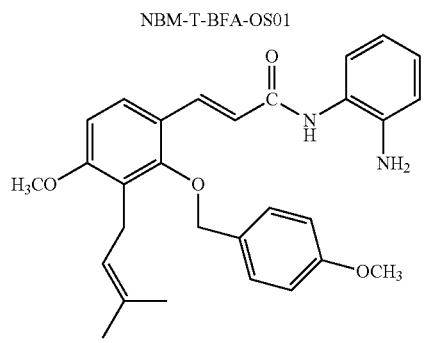
NBM-T-BMA-OS01
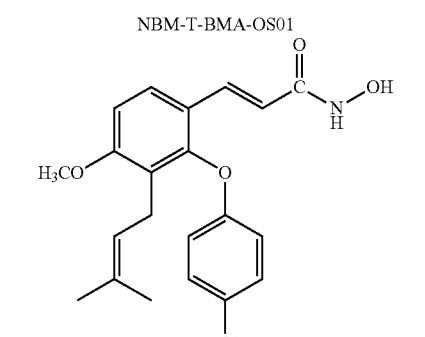
NBM-T-BCX-OS01

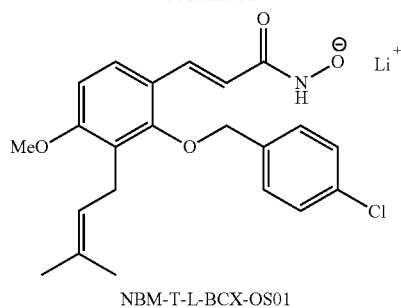
NBM-T-L-BCX-OS01
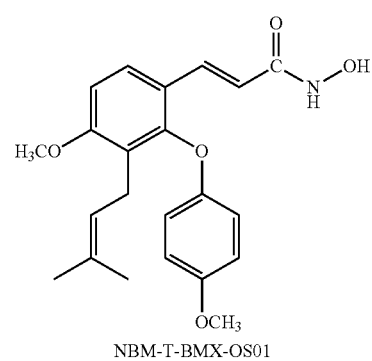
NBM-T-BMX-OS01
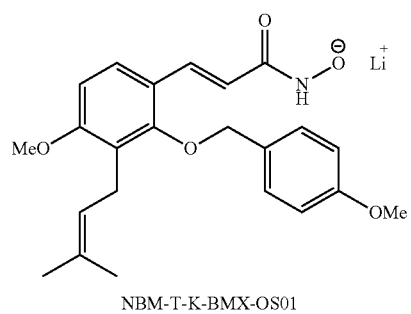
NBM-T-K-BMX-OS01
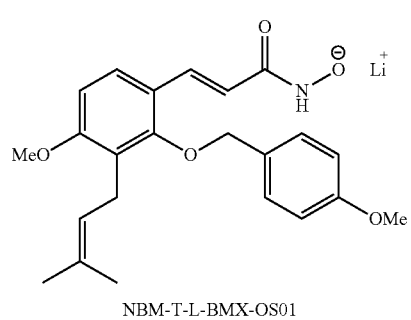
NBM-T-L-BMX-OS01
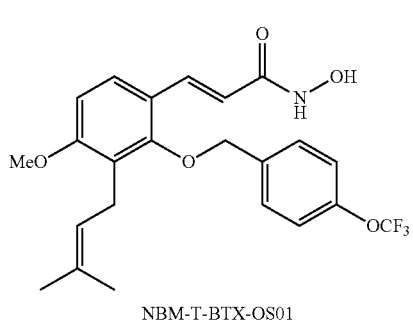
NBM-T-BTX-OS01
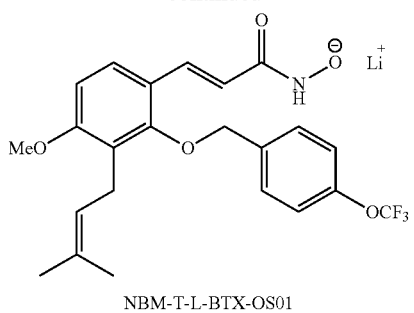
NBM-T-L-BTX-OS01
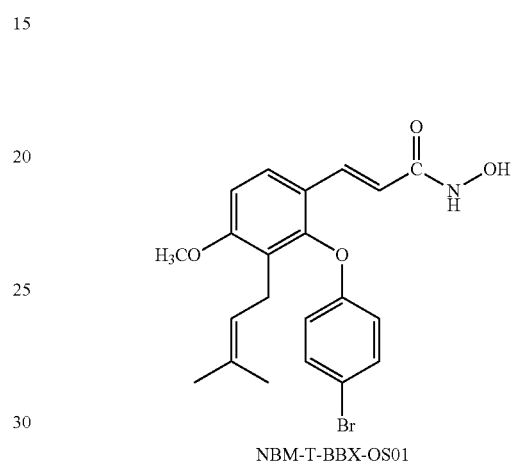
NBM-T-BBX-OS01
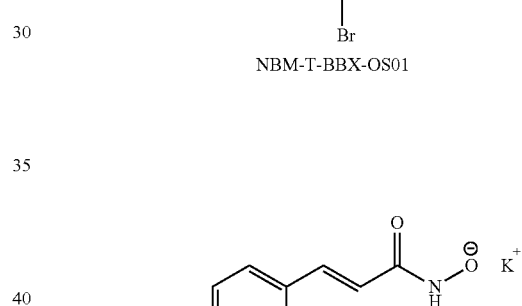
NBM-T-L-BBX-OS01
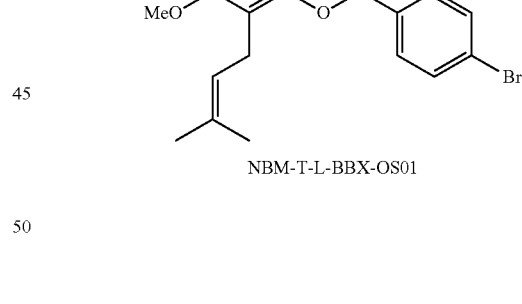
NBM-T-BFX-OS01

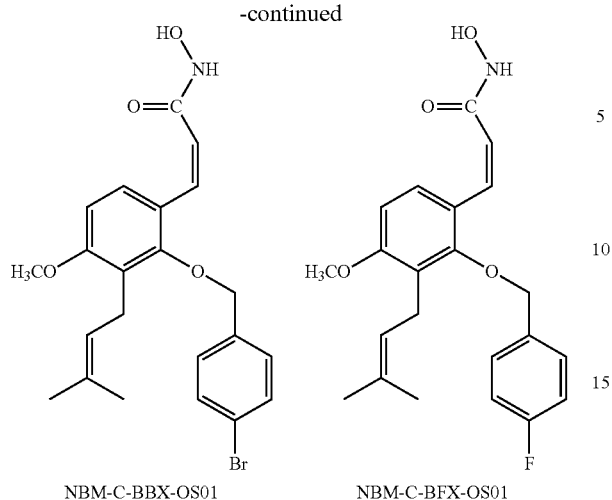
NBM-C-BBX-OS01   NBM-C-BFX-OS01
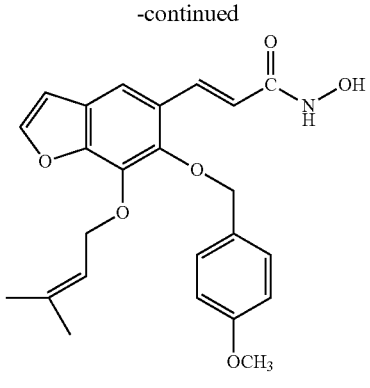
NBM-T-I-BMX-OS01
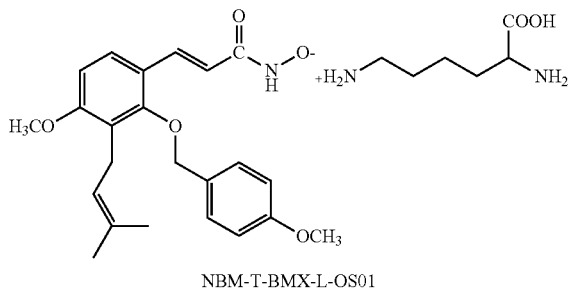
NBM-T-TMX-OS01
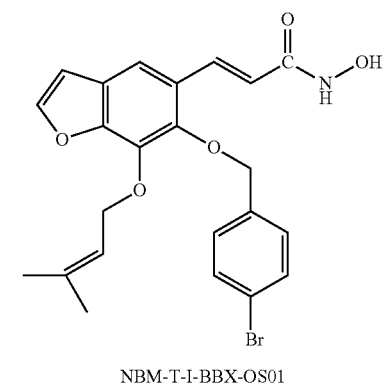
NBM-T-L-I-BMX-OS01
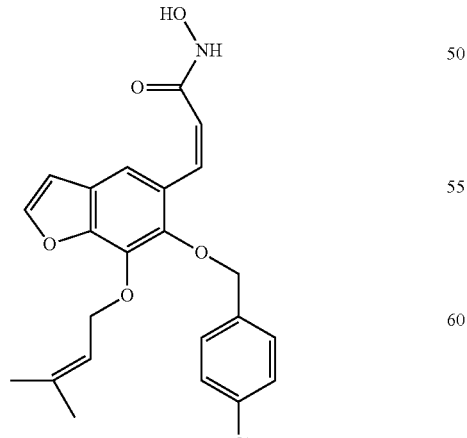
NBM-T-BMX-L-OS01
NBM-T-I-BBX-OS01
NBM-I-BCX-OS01
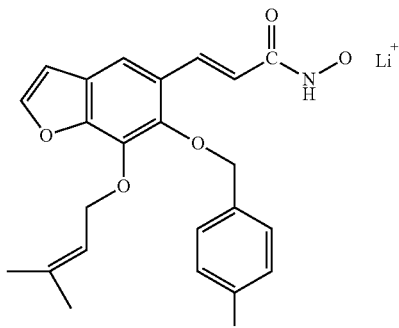
NBM-T-L-I-BBX-OS01

-continued

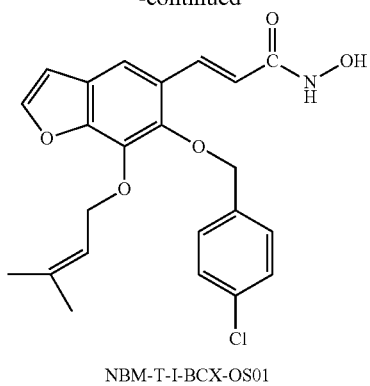

NBM-T-I-BCX-OS01

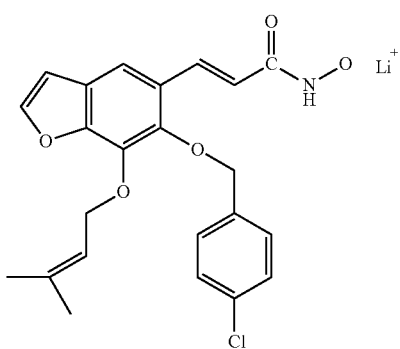

NBM-T-L-I-BCX-OS01

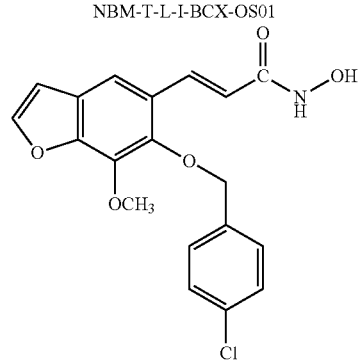

NBM-T-I-MCX-OS01

According to another embodiment of the invention, the HDAC inhibitor used herein is SAHA, propolis or propolins (such as propolins A to J). Preferably, the propolis is Taiwanese green propolis, propolin A, propolin B, propolin C, propolin D, propolin E, propolin F, propolin G, propolin H, propolin I, propolin J, SAHA, NBM-HD-1.

The invention unexpectedly found that the HDAC inhibitors can change a ratio of 68 kDa protein to 64 kDa protein of MRJP3 in royal jelly secreted by worker bees feeding the HDAC inhibitor thereon. It is suggested that the change is induced by the epigenetic modification, which can be supported by Janet S. Graham et al., T. J. Walton et al., Julie C. Kiefer, and Ahmad Miremadi et al. The larvae feeding on the above royal jelly have higher weight and larger size than the normal so that their development period is shorter. The pupa and queen bee developed the larvae also have higher weight and larger size higher. Such queen bees have higher egg production so that the number of bees and production of honey increase accordingly.

EXAMPLE

Example 1

Preparation of Taiwanese Green Propolis Extract and Propolins C and G

Taiwanese Green Propolis Extract 50 g of Taiwanese Green Propolis (TP) were extracted with 95% ethyl alcohol (250 mL×3), sonicated for 3 hrs, and stood for 21 hrs at 25° C. The ethanol extract after filtration was dried under reduced pressure to yield a brown gum (34.5 g), which was kept at −20° C. before use.

Propolin C 5 g of TP extract were fractionated through a Sephadex LH-20 column (Amersham Pharmacia Biotech AB, Uppsala, Sweden). Methanol was used as solvent for elution and six fractions were obtained. All eluates, including fractions from the follow-up chromatography, were chromatographed on a silica gel column using a gradient solvent system of n-hexane and EtOAc for elution. Purification of the most active fraction 4 (n-hexane: EtOAc, 70:30) was carried out by reversed-phase (RP) preparative high-performance liquid chromatography (HPLC)/UV. Fractions in the retention time at 45.0 min for propolin C were collected. Conditions used were as follows: column: Luna Phenomenex (C18, 250 mm×10 mm); solvent system: methanol: water (7:3); flow rate: 2.5 mL/min; and detection: UV 280 nm. The compound was identified as propolin C, and its purity was estimated to be no less than 95% by HPLC/UV based on the peak area.

Propolin G 5 g of TP extract were fractionated through a Sephadex LH-20 column (Amersham Pharmacia Biotech AB, Uppsala, Sweden). Methanol was use as the solvent for elution and six fractions were obtained. All eluates, including fractions from the follow-up chromatography, were chromatographed on silica gel column using a gradient solvent system of n-hexane and EtOAc for elution. Purification of the most active fraction 3 (n-hexane: EtOAc, 70:30) was carried out by a reversed-phase (RP) preparative high-performance liquid chromatography (HPLC)/UV. Fractions in retention time at 25.0 min for propolin G were collected. The conditions used were as follows: column: Luna Phenomenex (C18, 250 mm×10 mm); solvent system: methanol:water (8.5:1.5); flow rate: 3.5 mL/min; and detection: UV 280 nm. The compound was identified as propolin G, with purity estimated to be no less than 95% by HPLC/UV based on the peak area.

Example 2

Collection and Analysis of Royal Jelly and Larvae of the Queen Bee

Beehives with the similar expression level of MRJP3 protein were selected for use, and two beehives were tested in each control or experimental group. On the first day, the honey originally contained in the beehives was removed by shaking, and the bees (Apis mellifera) were fed sugar water twice (normal sugar water for the control group and special sugar water for the experimental group) for two days. The special sugar water was a 10-fold dilution of the formulated sugar powder in water. On the third day, 1.5-day old larvae (which were the offspring of the same queen) were inserted into the beehives, and the bees were fed once (normal sugar water for the control group and special sugar water for the experimental group). After 24, 48, and 72 hrs, 20 larvae and the royal jelly in the cells of said 20 larvae were collected for qualitative, quantitative, and proteomic analyses.

For qualitative analysis, royal jelly and sterilized water at a weight ratio of 1:10 was mixed for extraction. A particular amount of the proteins in the aqueous layer were removed for determination of protein concentration by Bradford dye-binding method (Bio-Rad protein assay, Bio-Rad Laboratories, Inc.). The absorption at 595 nm of the protein samples was determined by Elisa Reader (Bio-TEK). 10 µg of protein were placed on a 12.5% SDS-PAGE gel at 60 volts for 30 minutes and 120 volts for 2 hours to separate proteins of different molecular weights. The gel was stained by Coomassie blue (Commassie Brilliant Blue R, Sigma, B-0630) for 15 minutes and destained by destain buffer (methanol:acetic acid:ddH$_2$O at 20:7:73) so that the background of the gel became transparent.

The larvae were washed with 1×PBS so that residual royal jelly is removed from the larva body, and were then ground. After grinding, a suitable amount of sterilized water was added for protein extraction. A particular amount of the proteins in the aqueous layer were removed for determination of protein concentration by the method described above, and 10 µg of protein were placed on a 12.5% SDS-PAGE gel at 60 volts for 30 minutes and 120 volts for 2 hours to separate proteins of different molecular weights. The gel was stained by Coomassie blue (Commassie Brilliant Blue R, Sigma, B-0630) for 15 minutes and destained by destain buffer (methanol:acetic acid:ddH$_2$O at 20:7:73) so that the background of the gel became transparent.

For quantitative analysis, royal jelly and larvae of the queen bee in different hives in the control or experimental group at different time points (24, 48, or 72 hrs) were collected. Their weight was determined and the larvae were photographed for analysis and comparison.

For proteomic analysis and protein identification, suspension from the supernatant of the royal jelly or the larvae of the queen bee was vacuum-dried by a rotary evaporator (Speed Vac) and redissolved in rehydration buffer. The protein concentration was determined by Bradford dye-binding method. Afterwards, 10 µg of royal jelly and 100 µg of larvae of the queen bee were tested for a two-dimensional electrophoresis (2-DE) analysis by the following steps: the samples were first separated by isoelectric focusing (IEF) using a strip of pH 3 to 10 followed by equilibration, and then separated by sodium dodecyl sulfate-polyacrylamide gel electrophoresis (SDS-PAGE) (stacking gel: 30% Acrylamide (Bio-Rad), Tris pH6.8, 10% APS, ddH$_2$O, 1% SDS, TEMED; separating gel: 30% Acrylamide (Bio-Rad), Tris pH8.8, 10% APS, ddH$_2$O, 1% SDS, TEMED). The images of the gel were taken and analyzed by Image Master 2D Platinum 6.0 software. The spots of interest on the gel underwent in-gel trypsin digestion and were analyzed by mass spectrometer LC-ESI-Q-TOF MS/MS. The data obtained were then compared against the database for protein identification by Mascot software.

Example 3

Figure 1:
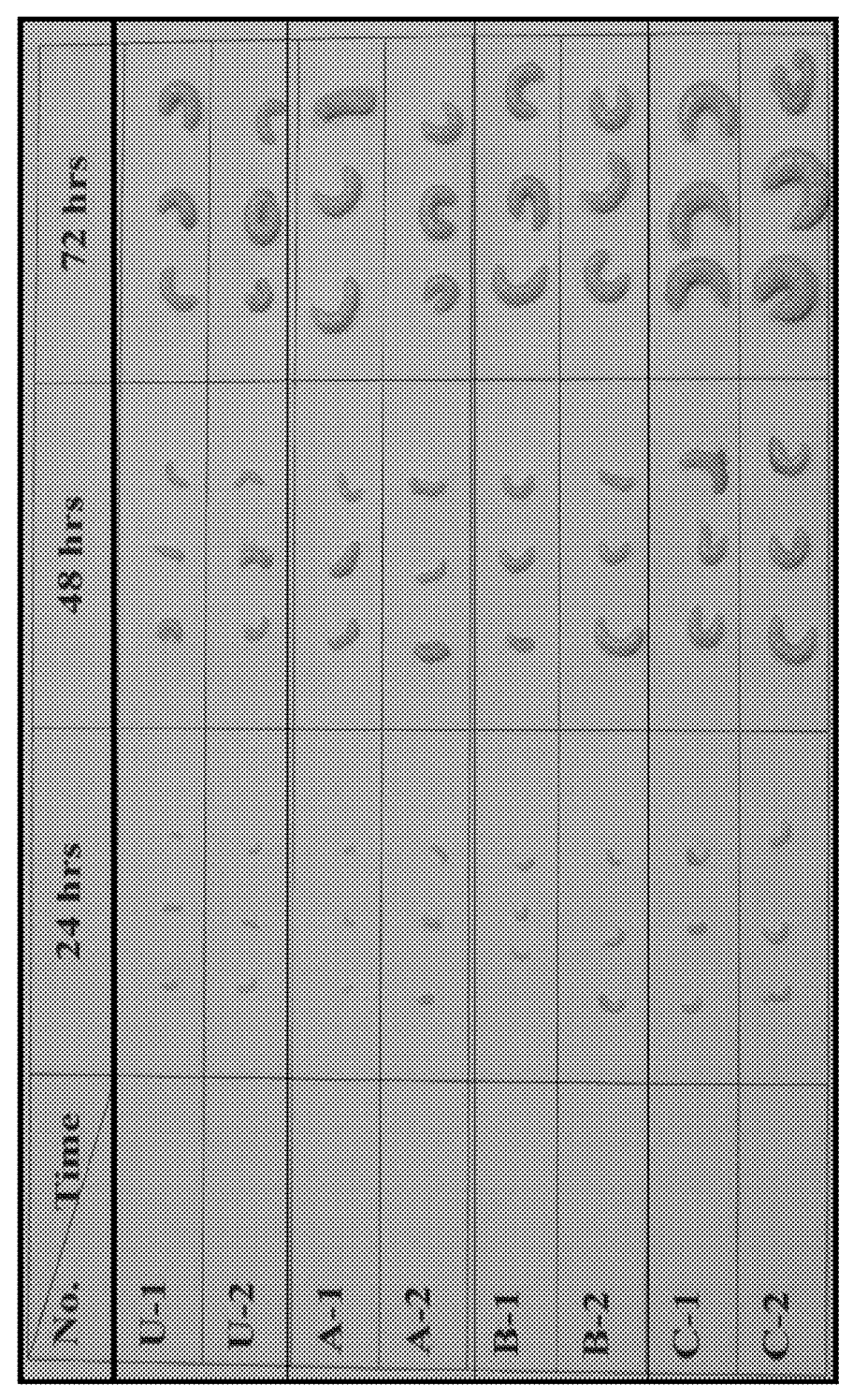

Effects of Taiwanese Green Propolis Extract in Inducing Growth of Larvae 10 kinds of propolins, namely propolins A to J, have been found in Taiwanese Green Propolis ethanol extract, and propolins C, D, F, and G are the major species. Bees were fed sugar water containing 1.25, 2.5, and 5.0 g of Taiwanese Green Propolis extract per kg of sugar three times, and the larvae of the queen bee and the royal jelly produced by the worker bees were collected 24, 48, and 72 hrs after the insertion of the 1.5-day old larvae for analysis. As shown in Table 1 and FIG. 1, 1.25 to 5.0 g/kg of Taiwanese Green Propolis extract significantly promoted the growth of the larvae. During the period of 24 to 48 hrs, the larvae of the control group grew from 4.73 mg to 12.26 mg, as the weight increased around 1.59 fold. Meanwhile, the larvae of the group treated with a high dose of Taiwanese Green Propolis extract (5 g/kg) grew from 6.78 mg to 26.72 mg, as the weight increased around 2.94 fold. During the period of 48 to 72 hrs, the larvae of the control group grew from 12.26 mg to 31.70 mg, as the weight increased around 1.58 fold. Meanwhile, the larvae of the group treated with a high dose of Taiwanese Green Propolis extract (5 g/kg) grew from 26.72 mg to 107.55 mg, as the weight increased around 3.03 fold.

TABLE 1

Special royal jelly secreted by young worker bees fed on Taiwanese Green Propolis extract induced rapid growth of larvae

| Average weight of each larva (mg) | Collection time | | |
|---|---|---|---|
| Group | 24 h | 48 h | 72 h |
| control (U-1 and 2) | 4.73 ± 0.54 | 12.26 ± 0.74 | 31.70 ± 11.08 |
| Taiwanese Green Propolis extract-low dose (A-1 and 2) (1.25 g/kg) | 5.05 ± 2.19 | 12.43 ± 3.52 | 60.71 ± 6.56 |
| Taiwanese Green Propolis extract-medium dose (B-1 and 2) (2.5 g/kg) | 6.86 ± 1.14 | 11.77 ± 0.97 | 51.16 ± 11.61 |
| Taiwanese Green Propolis extract-high dose (C-1 and 2) (5.0 g/kg) | 6.78 ± 1.37 | 26.72 ± 4.29 | 107.55 ± 3.47 |

The above data show that feeding bees with sugar-containing Taiwanese Green Propolis extract results in the production of special royal jelly by worker bees, and the larvae fed on said special royal jelly in turn exhibit rapid growth.

The special royal jelly was further analyzed to determine whether it differs from normal royal jelly in quantity or quality. According to the data that we obtained, the yield of the special royal jelly (obtained from the treated groups) was not significantly different from that of normal royal jelly (obtained from the control group) (see Table 2). The young worker bees did provide sufficient royal jelly for the larvae according to the larvae's sizes and consumption.

TABLE 2

Taiwanese Green Propolis extract did not significantly affect the yield of royal jelly secreted by young worker bees

| (g/20 wells) | Collection time | | |
|---|---|---|---|
| Group | 24 h | 48 h | 72 h |
| control (U-1 and 2) | 3.375 ± 0.7 | 9.19 ± 1.1 | 11.96 ± 0.83 |
| Taiwanese Green Propolis extract-low dose (A-1 and 2) (1.25 g/kg) | 3.03 ± 0.58 | 8.30 ± 0.81 | 12.1 ± 1.0 |

TABLE 2-continued

Taiwanese Green Propolis extract did not significantly affect the yield of royal jelly secreted by young worker bees

| (g/20 wells) | Collection time | | |
|---|---|---|---|
| Group | 24 h | 48 h | 72 h |
| Taiwanese Green Propolis extract-medium dose (B-1 and 2) (2.5 g/kg) | 2.04 ± 0.50 | 6.50 ± 0.69 | 10.21 ± 1.08 |
| Taiwanese Green Propolis extract-high dose (C-1 and 2) (5.0 g/kg) | 3.09 ± 0.59 | 8.76 ± 1.21 | 13.12 ± 2.38 |

The amounts of water-soluble proteins in normal royal jelly and the special royal jelly were also compared, and no significant difference was identified (see Table 3). The result indicates that Taiwanese Green Propolis extract only has impact on the ratio of the expression level of the different isoforms of the MRJP3 protein but does not induce synthesis of new proteins. In other words, the amount of total proteins does not change.

TABLE 3

Taiwanese Green Propolis extract did not significantly affect the amount of the water-soluble proteins in royal jelly secreted by young worker bees mg

| water-soluble protein/g royal jelly | Collection time | | |
|---|---|---|---|
| Group | 24 h | 48 h | 72 h |
| control (U-1 and 2) | 48.94 ± 0.29 | 38.37 ± 0.29 | 41.02 ± 9.20 |
| Taiwanese Green Propolis extract-low dose (A-1 and 2) (1.25 g/kg) | 44.47 ± 4.89 | 29.43 ± 6.04 | 32.68 ± 1.44 |
| Taiwanese Green Propolis extract-medium dose (B-1 and 2) (2.5 g/kg) | 46.91 ± 3.16 | 38.78 ± 5.46 | 34.51 ± 2.30 |
| Taiwanese Green Propolis extract-high dose (C-1 and 2) (5.0 g/kg) | 37.76 ± 16.10 | 33.70 ± 0.57 | 36.34 ± 2.59 |

It was also found that consumption of the special royal jelly not only induced rapid growth of the larvae of the queen bee but also increased the protein level in these larvae (see Table 4). It seemed that the protein level increased in proportion to the weight increase identified in these larvae (see Table 1).

TABLE 4

Taiwanese Green Propolis extract resulted in increase of protein level in larvae

| μg total protein/larva | Collection time | | |
|---|---|---|---|
| Group | 24 h | 48 h | 72 h |
| control (U-1 and 2) | 60.9 ± 24.89 | 383.35 ± 39.24 | 1595.05 ± 349.24 |
| Taiwanese Green Propolis extract-low dose (A-1 and 2) (1.25 g/kg) | 80.4 ± 14.85 | 557.7 ± 268.42 | 1397.55 ± 122.26 |
| Taiwanese Green Propolis extract-medium dose (B-1 and 2) (2.5 g/kg) | 165.25 ± 9.12 | 639.5 ± 61.09 | 2922.2 ± 776.97 |
| Taiwanese Green Propolis extract-high dose (C-1 and 2) (5.0 g/kg) | 193.95 ± 48.01 | 1393.2 ± 30.55 | 4679.05 ± 436.50 |

Example 4

Effects of Propolin C on Growth of Larvae

Propolin C is the major ingredient of Taiwanese Green Propolis, and it is also the most abundant species among all propolins. By carrying out the experimental methods described above, it was found that treatment of 50 to 100 mg/kg of propolin C significantly changed the protein components of the royal jelly secreted by young worker bees and induced rapid growth of the larvae fed on the above royal jelly (see Table 5 and FIG. 2). It seemed that in order to promote the growth of larvae that the dose of propolin C should have been adjusted to 300 mg/kg. According to the data, during the period of 48 to 72 hours, the larvae of the control group grew from 13.45 mg to 61.60 mg, as the weight increased around 3.58 fold. Meanwhile, the larvae of the group treated with a high dose of propolin C (100 mg/kg) grew from 13.48 mg to 98.48 mg, as the weight increased around 6.30 fold.

TABLE 5

Special royal jelly secreted by young worker bees fed on propolin C induced rapid growth of larvae

| Average weight of each larva (mg) | Collection time | | |
|---|---|---|---|
| Group | 24 h | 48 h | 72 h |
| control (U-2) | 3.52 | 13.45 | 61.60 |
| Propolin C (C1-2) (50 mg/kg) | 2.40 | 15.2 | 70.17 |
| Propolin C (C2-2) (100 mg/kg) | 2.38 | 13.48 | 98.48 |

Example 5

Figure 3:
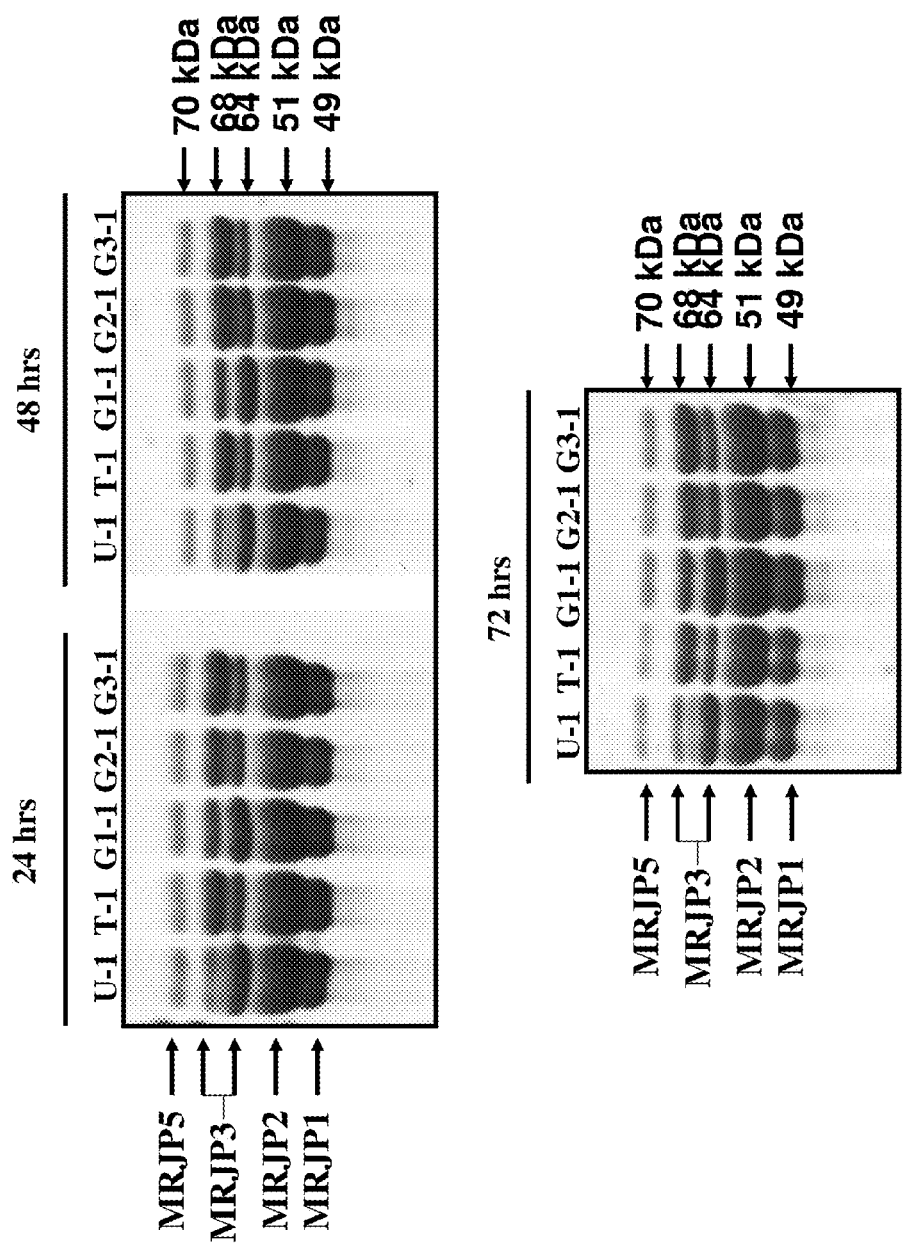
FIG. 3 shows the water-soluble protein components identified in the royal jelly secreted by young worker bees fed on propolin G. The samples were collected at different time points. U-1: control group; T-1: positive control group treated with 5.0 g/kg of Taiwanese Green Propolis extract; G1-1: treated with 150 mg/kg of propolin G; G2-1: treated with 300 mg/kg of propolin G; G3-1: treated with 600 mg/kg of propolin G.

Effects of Propolins D, F, and G on Expression of MRJP3 Protein and Growth of Larvae Propolins D, F, and G are also major ingredients of Taiwanese Green Propolis. In our study, bees were fed sugar water containing 150, 300, and 600 mg of propolin G per kg of sugar three times, and the larvae of the queen bee and the royal jelly produced by the worker bees were collected 24, 48, and 72 hrs after the insertion of the 1.5-day old larvae for analysis. As shown in FIG. 3, the expression of the water-soluble protein MRJP3 in the special royal jelly (from the experimental/treated groups) significantly differed from that of normal royal jelly (from the control group). At 72 hrs, the 68 and 64 kDa MRJP3 in the control group were of a ratio of 2:8, whereas those in the group treated with a medium dose (300 mg/kg) of propolin G were of a ratio of 6.5:3.5. Clearly, the expression of the 68 kDa MRJP3 proteins increased and 64 kDa MRJP3 proteins decreased significantly.

Regarding the effect of the special royal jelly secreted by young worker bees fed on propolin G on the growth of larvae, it was found that during the period of 24 to 48 hours, the larvae of the control group grew from 5.23 mg to 13.57 mg, as the weight increased around 1.60 fold. The larvae of the positive control group treated with a high dose of Taiwanese Green Propolis extract (5 g/kg) grew from 5.53 mg to 30.27 mg, as the weight increased around 4.47 fold. Meanwhile, the larvae of the group treated with 300 mg/kg of propolin G grew from 3.93 mg to 23.80 mg, as the weight increased around 5.05 fold. During the period of 48 to 72 hours, the larvae of the control group grew from 13.57 mg to 30.07 mg, as the weight increased around 1.22 fold. The larvae of the positive control group treated with a high dose of Taiwanese Green Propolis extract (5 g/kg) grew from 30.27 mg to 103.30 mg, as the weight increased around 2.41 fold. Meanwhile, the larvae of the group treated with 300 mg/kg of propolin G grew from 23.80 mg to 161.73 mg, as the weight increased around 5.79 fold (see Table 6).

TABLE 6

Special royal jelly secreted by young worker bees fed on propolin G induced rapid growth of larvae

| Average weight of each larva (mg) | Collection time | | |
|---|---|---|---|
| group | 24 h | 48 h | 72 h |
| control (U-1) | 5.23 | 13.57 | 30.07 |
| Taiwanese Green Propolis extract-high dose (T-1) (5 g/kg) | 5.53 | 30.27 | 103.30 |
| Propolin G (G1-1) (150 mg/kg) | 5.73 | 54.2 | 156.63 |
| Propolin G (G2-1) (300 mg/kg) | 3.93 | 23.80 | 161.73 |
| Propolin G (G3-1) (600 mg/kg) | 2.70 | 13.67 | 85.67 |

The above data imply that the special royal jelly is better nutritiously formulated and thus is capable of inducing rapid growth of larvae.

Propolins D and F were also found to result in similar effects. However, the effects were less significant.

Example 6

Figure 4:
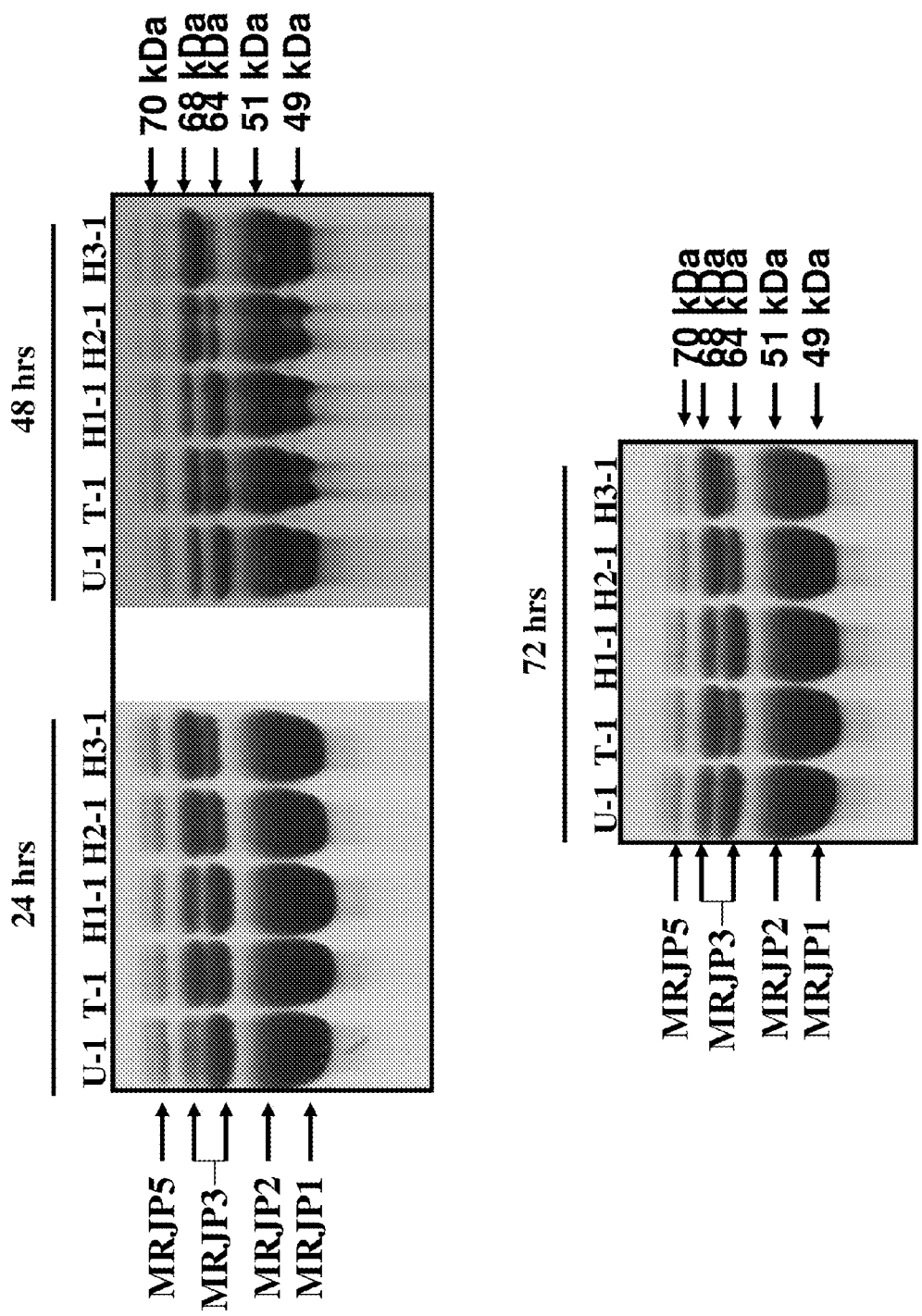
FIG. 4 shows the water-soluble protein components identified in the royal jelly secreted by young worker bees fed on NBM-HD-1. The samples were collected at different time points. U-1: control group; T-1: positive control group treated with 5.0 g/kg of Taiwanese Green Propolis extract; H1-1: treated with 50 mg/kg of NBM-HD-1; H2-1: treated with 100 mg/kg of NBM-HD-1; H3-1: treated with 200 mg/kg of NBM-HD-1.

Effects of new HDAC Inhibitor NBM-HD-1 on Expression of MRJP3 Protein and Growth of Larvae NBM-HD-1 derives from the synthesis of propolin G, and is known to be a new histone deacetylase (HDAC) inhibitor. By carrying out the experimental methods described above, it was found that treatment of 50 to 200 mg/kg of NBM-HD-1 significantly changed the ratio of the protein components of the royal jelly secreted by young worker bees. For instance, at 72 hrs, the 68 and 64 kDa MRJP3 in the control group were of a ratio of 4:6, whereas those in the group treated with a high dose (5 g/kg) of Taiwanese Green Propolis extract (i.e., the positive control group) were of a ratio of 7:3. Meanwhile, the 68 kDa and 64 kDa MRJP3 in the group treated with 200 mg/kg of NBM-HD-1 were of a ratio of 9:1 (see FIG. 4).

Moreover, as shown in Table 7, treatment of NBM-HD-1 induced rapid growth of the larvae.

TABLE 7

Special royal jelly secreted by young worker bees fed on NBM-HD-1 induced rapid growth of larvae

| Average weight of each larva (mg) | Collection time | | |
|---|---|---|---|
| Group | 24 h | 48 h | 72 h |
| control (U-1) | 2.2 | 7.8 | 19.3 |
| Taiwanese Green Propolis extract-high dose (T-1) (5 g/kg) | 2.8 | 12.7 | 51.9 |
| NBM-HD-1 (H1-1) (50 mg/kg) | 4.57 | 18.0 | 37.4 |
| NBM-HD-1 (H2-1) (100 mg/kg) | 3.5 | 14.3 | 79.9 |
| NBM-HD-1 (H3-1) (200 mg/kg) | 2.1 | 17.8 | 82.6 |

The above data suggests that change of protein ratio between the different isoforms of MRJP3 protein results in rapid growth of the larvae of the queen bee, as demonstrated by the increase in the larva weight.

Figure 5:
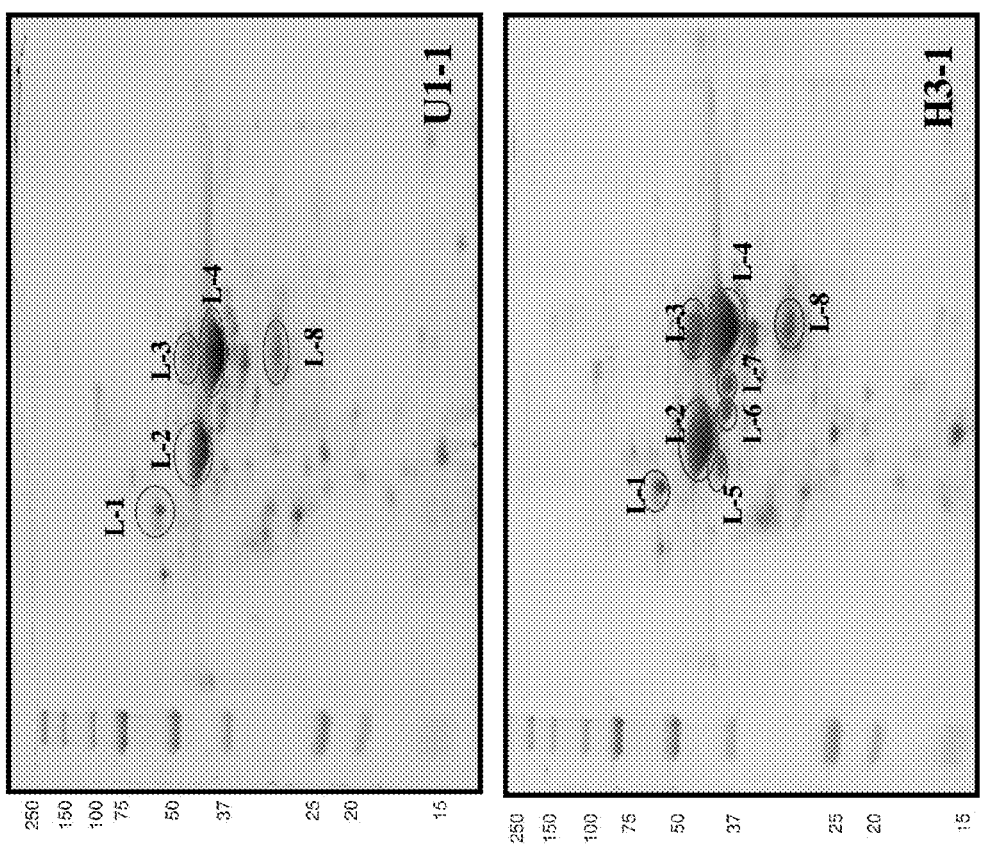
FIG. 5 shows the results of the two-dimensional gel electrophoresis analysis of the water-soluble proteins extracted from the larvae at 72 hrs from the group treated with NBM-HD-1. L-1: MRJP1; L-2: MRJP3; L-3: MRJP2, L-4: MRJP2; L-5: MRJP3; L-6: MRJP3; L-7: MRJP3; L-8: MRJP2. U1-1: control group; H3-1: treated with 200 mg/kg of NBM-HD-1.

When analyzing by 2-D gel electrophoresis and high resolution mass spectrometry the water-soluble proteins expressed in the larvae from different control and experimental groups, increase in the protein level of MRJPs 1, 2, and 3 (especially MRJP3) in the larvae from the group treated with NBM-HD-1 was demonstrated (see FIG. 5).

Example 7

Figure 6:
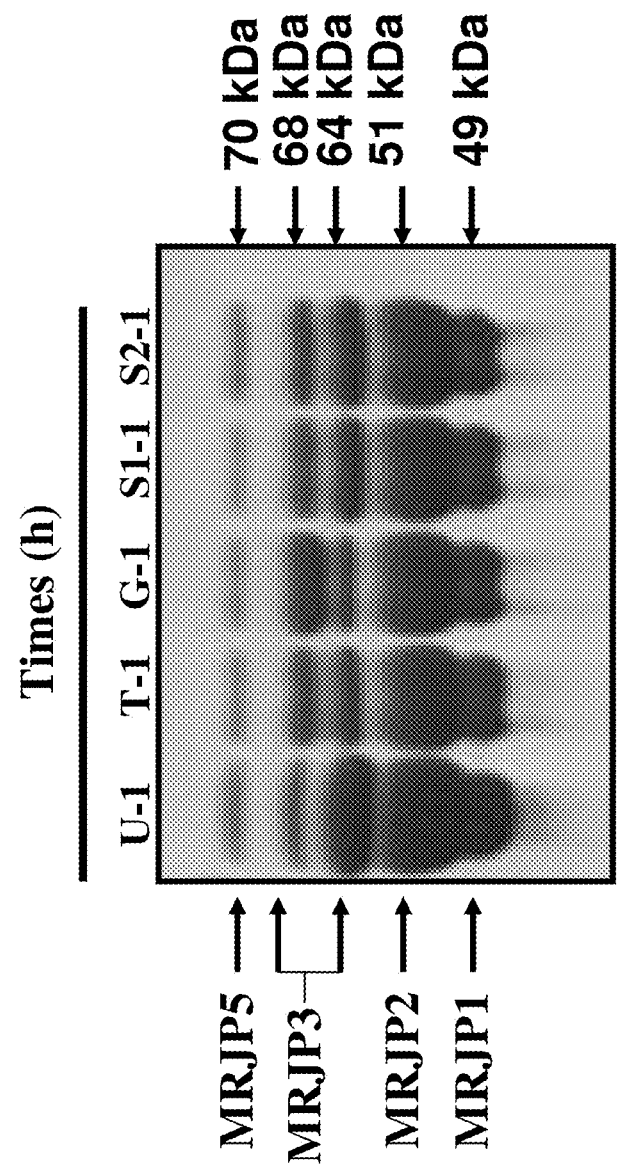
FIG. 6 shows the water-soluble protein components identified in the royal jelly secreted by young worker bees fed on SAHA. The samples were collected at time point of 72 hrs. U-1: control group; T-1: positive control group treated with 5.0 g/kg of Taiwanese Green Propolis extract; G-1: positive control group treated with 150 mg/kg of propolin G; S1-1: treated with 5 mg/kg of SAHA; S2-1: treated with 15 mg/kg of SAHA.

Effects of HDAC Inhibitor SAHA on Expression of MRJP3 Protein and Growth of Larvae SAHA is a very effective HDAC inhibitor. Under treatment with 5 to 15 mg/kg of SAHA, the ratio of the protein components of the royal jelly secreted by young worker bees significantly changed. For instance, at 72 hrs, the 68 and 64 kDa MRJP3 in the control group were of a ratio of 2:8, whereas those in the group treated with a high dose (5 g/kg) of Taiwanese Green Propolis extract and 150 mg/kg of propolin G (i.e., the positive control groups) were of a ratio of 5.5:4.5 and 8:2, respectively. Meanwhile, the 68 kDa and 64 kDa MRJP3 in the group treated with 15 mg/kg of SAHA were of a ratio of 4:6 (see FIG. 6).

TABLE 8

Special royal jelly secreted by young worker bees fed on SAHA induced rapid growth of larvae

| Average weight of each larva (mg) | Collection time | | |
|---|---|---|---|
| group | 24 h | 48 h | 72 h |
| control (U-1) | 1.9 | 13.3 | 38.4 |
| Taiwanese Green Propolis extract-high dose (T-1) (5 g/kg) | 2.9 | 24.1 | 194.7 |
| Propolin G (G-1) (150 mg/kg) | 3.6 | 41.2 | 178.6 |
| SAHA (S1-1) (5 mg/kg) | 4.0 | 28.2 | 149.3 |
| SAHA (S2-1) (15 mg/kg) | 7.3 | 41.0 | 149.2 |

Example 8

Development of Special Queen Bee

Figure 9:
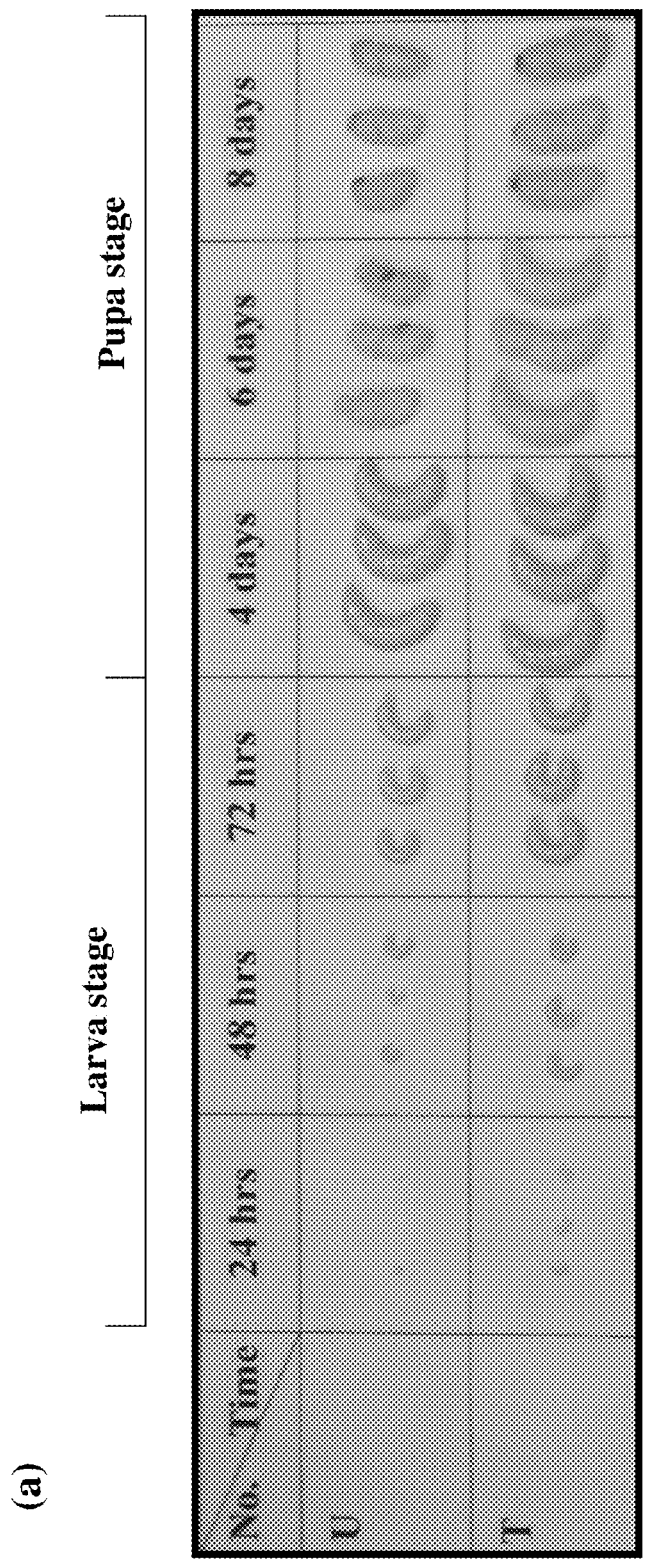
FIGS. 9 (a) to (c) demonstrate that Taiwanese Green Propolis extract induced young worker bees to secrete special royal jelly which was capable of promoting growth and development of the larvae of the queen bee. U: control group; T: treated with 5.0 g/kg of Taiwanese Green Propolis extract.
Figure 9:
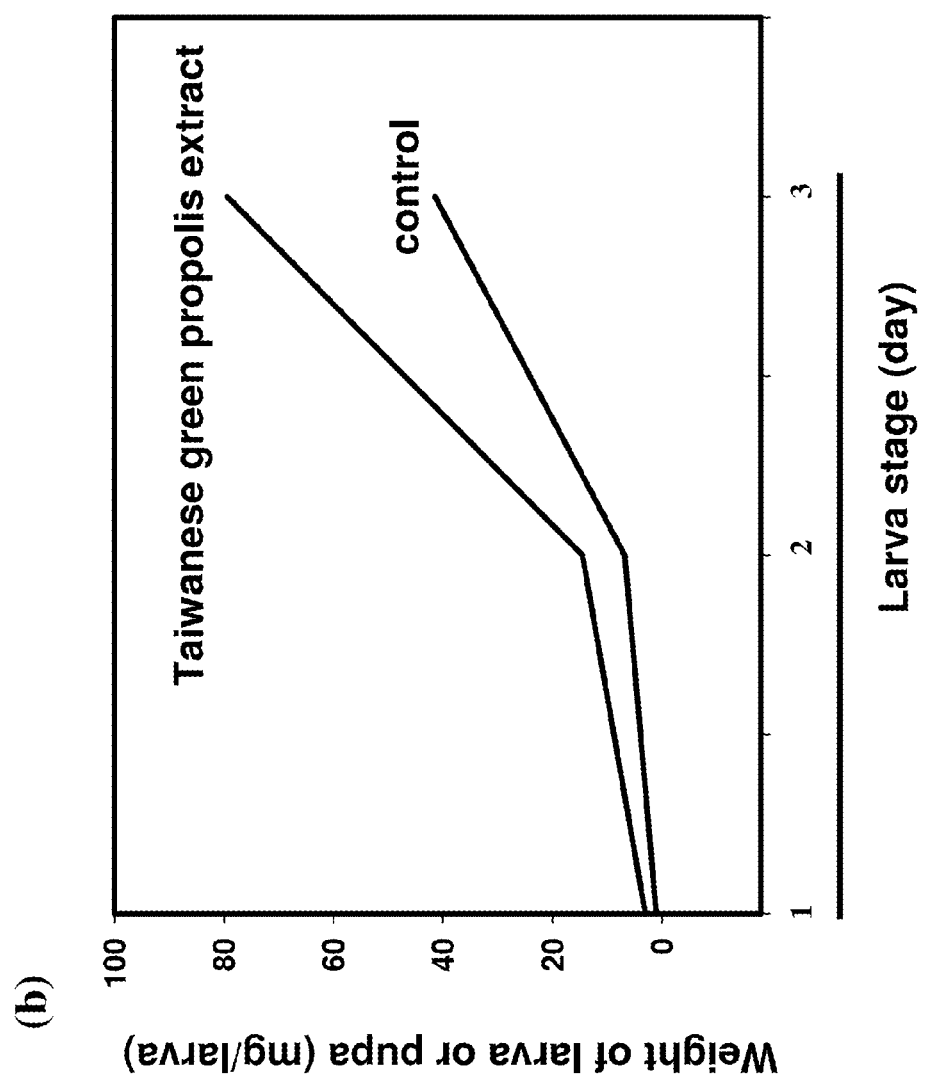
Figure 9:
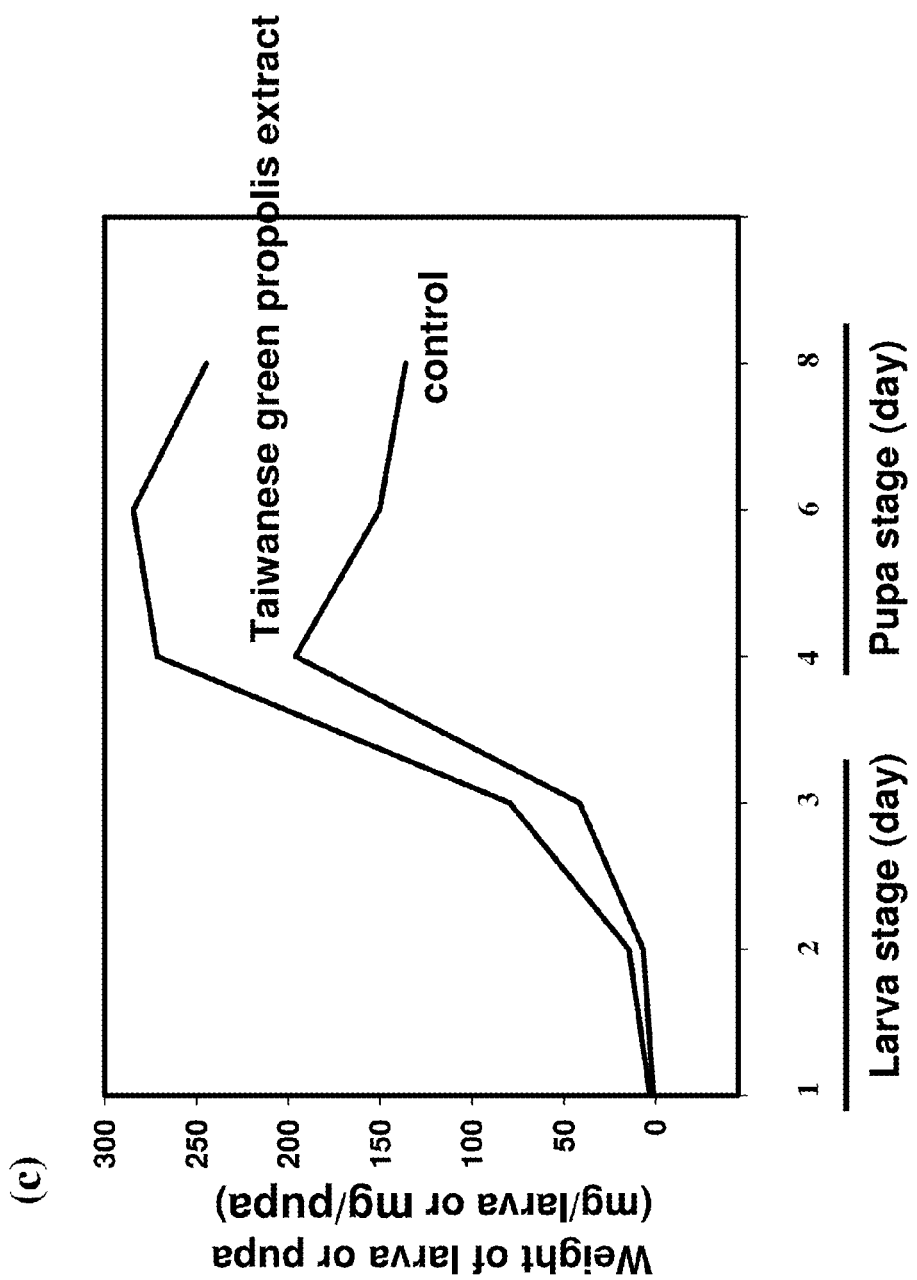

Experiments were carried out to study the development and metamorphosis of the larvae fed on the special royal jelly secreted by young worker bees fed on Taiwanese Green Propolis extract. As previously demonstrated, treatment with Taiwanese Green Propolis extract significantly promoted growth of larvae during the larva stage. As the larvae developed, it was found that at the pupa stage, pupas on the $4^{th}$ day to the $8^{th}$ day from the experimental group (treated with 5.0 g/kg of Taiwanese Green Propolis extract) were clearly of bigger sizes than those from the control group (see FIG. 9 (a)). When the weight of the larvae and pupas was measured, it was found that the larvae on the third day (of the larva stage) from the experimental group were around 100% heavier than those of the control group (see FIG. 9 (b)). At the pupa stage, the weight of the pupas on the $4^{th}$ and $8^{th}$ day dropped from 196.0 mg to 136.10 mg (per pupa) in the control group (around 30% decrease), whereas that of the experimental group dropped from 271.30 mg to 244.53 mg (per pupa) (around 9.8% decrease) (see FIG. 9 (c)). Clearly, pupas from the experimental group treated with Taiwanese Green Propolis extract consumed less energy during metamorphosis. It was also found that the pupas on the $8^{th}$ day from the experimental group were around 80% heavier than those from the control group, which is in accordance with the 100% weight difference between the control and experimental groups at the larva stage described above.

Example 9

Biological Functions of Our Special Royal Jelly

We investigated the role of the special royal jelly secreted by young worker bees fed on Taiwanese Green Propolis extract in anti-cancer function and neural stem cell differentiation.

Figure 7:
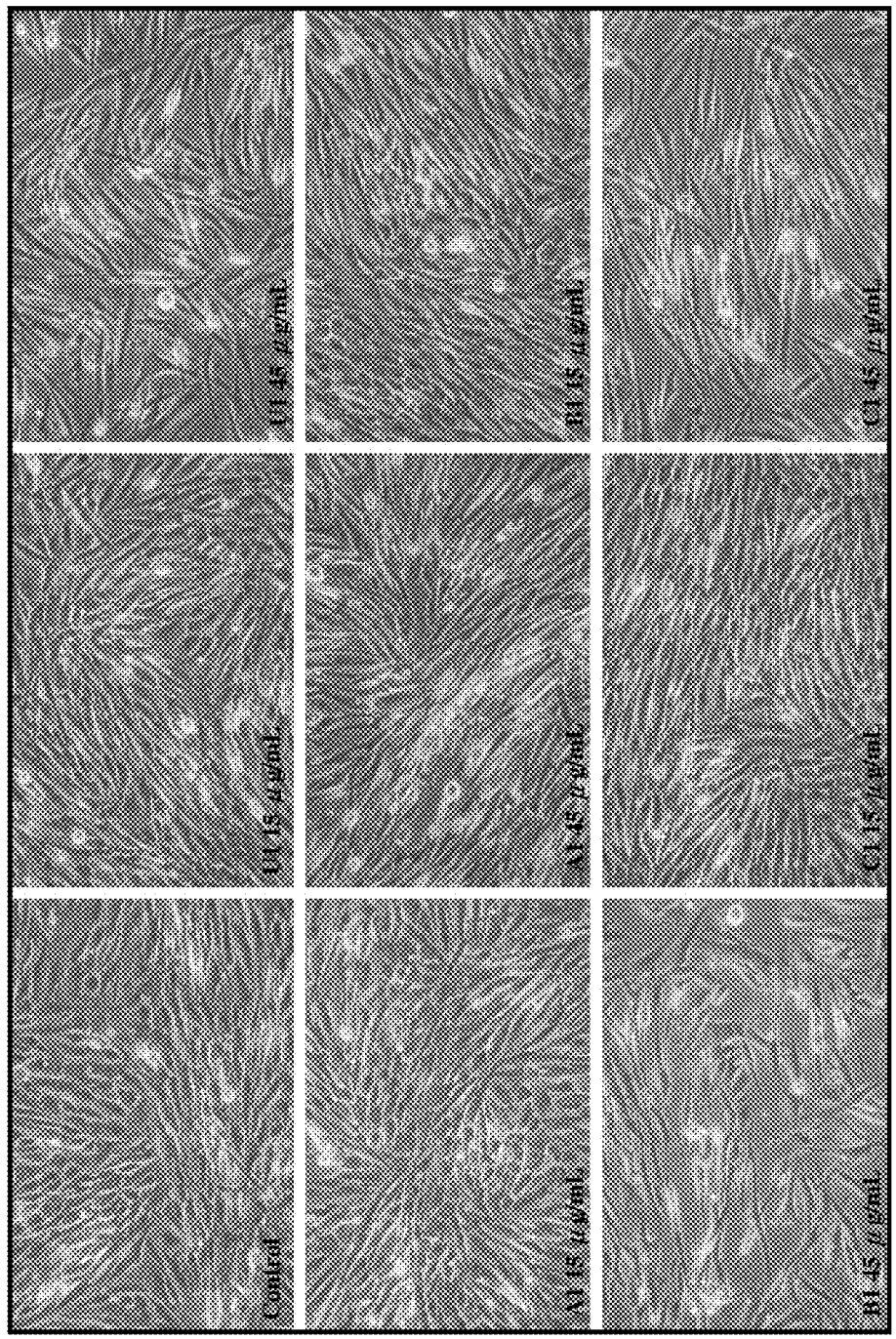
FIG. 7 demonstrates that Taiwanese Green Propolis extract induced young worker bees to secrete special royal jelly which was capable of inhibiting proliferation of human glioma Hs683 cells. U1: control group; A1: treated with 1.25 g/kg of Taiwanese Green Propolis extract; B1: treated with 2.50 g/kg of Taiwanese Green Propolis extract; C1: treated with 5.0 g/kg of Taiwanese Green Propolis extract.

In the anti-cancer study, Hs683 cells (human glioma cells) purchased from the Food Industry Research and Development Institute (Hsinchu, Taiwan) were cultured in RPMI 1640 (Gibco) with 2 mM glutamine and 0.1 mM NEAA, 100 mg/L of sodium pyruvate, 10% FBS, and a 1% dilution of penicillin and streptomycin, and maintained at 37° C. in a humidified atmosphere of 95% air and 5% $CO_2$. Cells ($3\times10^5$ per dish) were cultured in a 6-well dish and incubated overnight before switched to serum-starvation medium and treatment with different concentrations of water-soluble royal jelly protein (15 and 45 µg/mL) for 4 DIV. 5 ng/mL of EGF were used as the positive control. It was found that treatment with 45 µg/mL of royal jelly protein for 48 hrs significantly inhibited growth of Hs683 cells in groups B1 and C1 (see FIG. 7).

Figure 8:
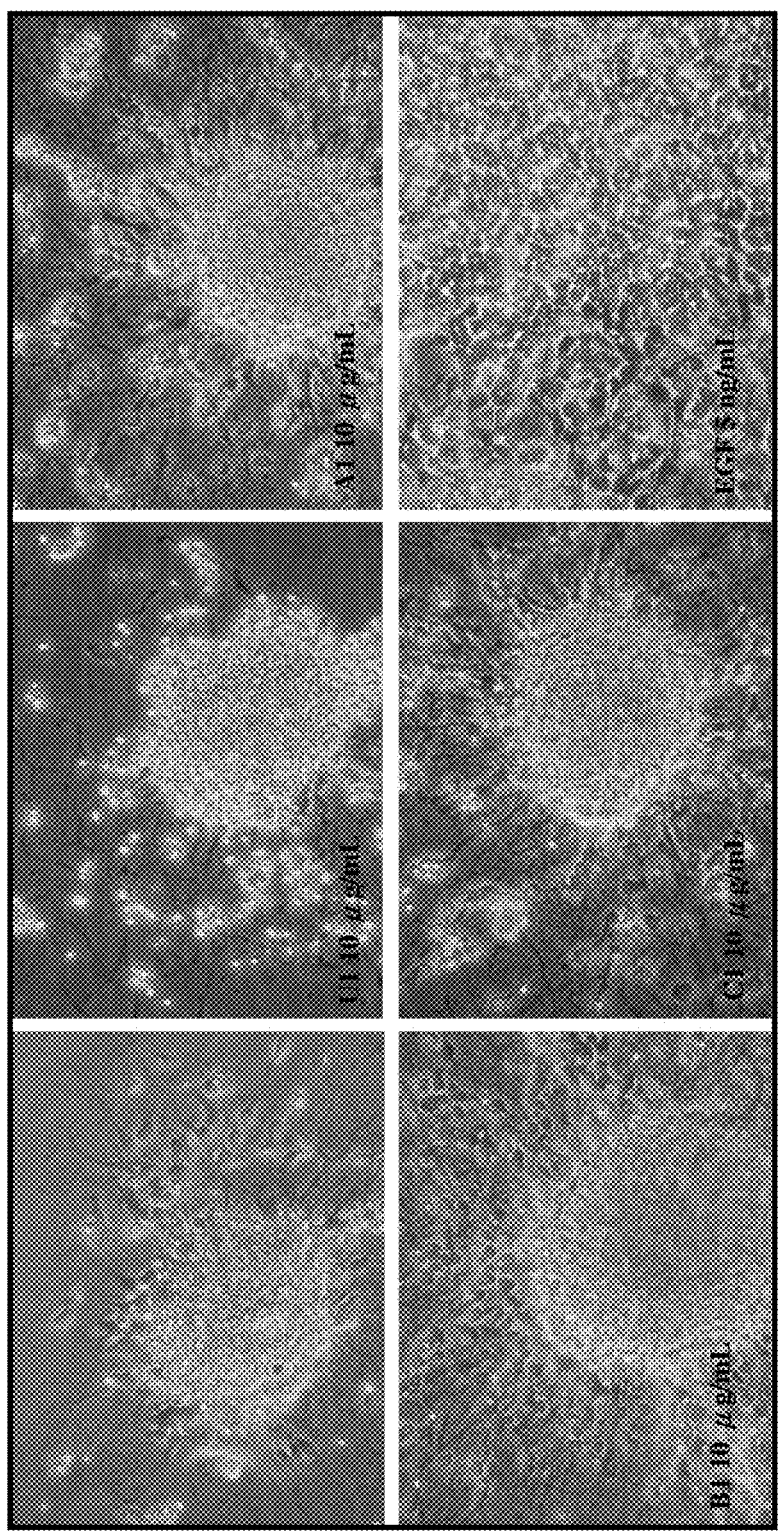
FIG. 8 demonstrates that Taiwanese Green Propolis extract induced young worker bees to secrete special royal jelly which was capable of inducing differentiation of rat neuronal stem cells. U1: control group; A1: treated with 1.25 g/kg of Taiwanese Green Propolis extract; B1: treated with 2.50 g/kg of Taiwanese Green Propolis extract; C1: treated with 5.0 g/kg of Taiwanese Green Propolis extract; EGF: positive control.

In the differentiation study, neural stem cells were cultured in neural-basal medium (Gibco) with B27 (Gibco), and maintained at 37° C. in a humidified atmosphere of 95% air and 5% $CO_2$ for 4 DIV. Neurospheres were treated with 10 µg/mL of water-soluble royal jelly protein for 3 DIV. EGF (5 ng/mL) served as the positive control. As shown in FIG. 8, treatment of 10 µg/mL of royal jelly protein for 72 hrs clearly induced differentiation of neural stem cells into neuronal cells, gliocytes, and oligodendrocytes in groups B1 and C1.

The above data suggest that HDAC inhibitors are capable of affecting chromatin remodeling in the hypopharyngeal and mandibular glands of young worker bees, and thus change the expression of the 68 and 64 kDa MRJP3 proteins without changing the expression of other MRJP proteins. Changes in the ratio between 68 and 64 kDa MRJP proteins can be identified in each enlarged larva, and the shift can be toward either the 68 kDa or the 64 kDa MRJP3 isoform. It is assumed that alternative splicing of polymorphic MRJP3 can be influenced by HDAC inhibitors, which in turn results in change of the expression of the 68 and 64 kDa isoforms. Regulation of the expression of the two isoform proteins thus determines the growth of larvae.

REFERENCES

1. Hellner M, Winter D, von Georgi R, Münstedt K. Apitherapy: usage and experience in german beekeepers. *Evid Based Complement Alternat Med.* 2008; 5(4):475-9.
2. Winston M L. The Biology of the Honeybee. Harvard University Press: Cambridge, Mass., 1987.
3. Robinson G E. In Neurobiology and Behavior of Honeybee; Menzel R, Mercer R, Eds.; Springer-Verlag: New Yorl, 1987; pp 266-279.
4. Peiren N, Vanrobaeys F, de Graaf D C, Devreese B, Van Beeumen J, Jacobs F J. The protein composition of honeybee venom reconsidered by a proteomic approach. *Biochim Biophys Acta.* 2005; 1752(1): 1-5.
5. Takaki-Doi S, Hashimoto K, Yamamura M, Kamei C. Antihypertensive activities of royal jelly protein hydrolysate and its fractions in spontaneously hypertensive rats. *Acta Med Okayama.* 2009; 63(1):57-64.
6. Mannoor M K, Shimabukuro I, Tsukamotoa M, Watanabe H, Yamaguchi K, Sato Y. Honeybee royal jelly inhibits autoimmunity in SLE-prone NZB×NZW F1 mice. *Lupus.* 2009; 18(1):44-52.
7. Gasic S, Vucevic D, Vasilijic S, Antunovic M, Chinou I, Colic M. Evaluation of the immunomodulatory activities of royal jelly components in vitro. *Immunopharmacol Immunotoxicol.* 2007; 29(3-4):521-36.
8. Vucevic D, Melliou E, Vasilijic S, Gasic S, Ivanovski P, Chinou I, Colic M. Fatty acids isolated from royal jelly modulate dendritic cell-mediated immune response in vitro. *Int Immunopharmacol.* 2007; 7(9):1211-20.
9. Boukraa L. Additive activity of royal jelly and honey against *Pseudomonas aeruginosa. Altern Med. Rev.* 2008; 13(4):330-3.
10. Hashimoto M, Kanda M, Ikeno K, Hayashi Y, Nakamura T, Ogawa Y, Fukumitsu H, Nomoto H, Furukawa S. Oral administration of royal jelly facilitates mRNA expression of glial cell line-derived neurotrophic factor and neurofilament H in the hippocampus of the adult mouse brain. *Biosci Biotechnol Biochem.* 2005; 69(4):800-5.
11. Guo H, Ekusa A, Iwai K, Yonekura M, Takahata Y, Morimatsu F. Royal jelly peptides inhibit lipid peroxidation in vitro and in vivo. *J Nutr Sci Vitaminol* (Tokyo). 2008; 54(3):191-5.
12. Scarselli R, Donadio E, Giuffrida M G, Fortunato D, Conti A, Balestreri E, Felicioli R, Pinzauti M, Sabatini A G, Felicioli A. Towards royal jelly proteome. *Proteomics.* 2005; 5(3):769-76.
13. Schmitzová J, Klaudiny J, Albert S, Schröder W, Schreckengost W, Hanes J, Júdová J, Simúth J. A family of major royal jelly proteins of the honeybee *Apis mellifera* L. *Cell Mol Life Sci.* 1998; 54(9):1020-30.
14. Kohno K, Okamoto I, Sano O, Arai N, Iwaki K, Ikeda M, Kurimoto M. Royal jelly inhibits the production of proinflammatory cytokines by activated macrophages. *Biosci Biotechnol Biochem.* 2004; 68(1):138-45.
15. Malecová B, Ramser J, O'Brien J K, Janitz M, Júdová J, Lehrach H, Simúth J. Honeybee (*Apis mellifera* L.) mrjp gene family: computational analysis of putative promoters and genomic structure of mrjp1, the gene coding for the most abundant protein of larval food. *Gene.* 2003; 303:165-75.
16. Furusawa T, Rakwal R, Nam H W, Shibato J, Agrawal G K, Kim Y S, Ogawa Y, Yoshida Y, Kouzuma Y, Masuo Y, Yonekura M. Comprehensive royal jelly (RJ) proteomics using one- and two-dimensional proteomics platforms reveals novel RJ proteins and potential phospho/glycoproteins. *J Proteome Res.* 2008; 7(8):3194-229.
17. Stefan Albert, Jaroslav Klaudiny, and Jozef Simuth., Molecular characterization of MRJP3, highly polymorphic protein of honeybee (*Apis mellifera*) royal jelly. *Insect Biochemistry and Molecular Biology* 29 (1999) 427-434.
18. Julie C. Kiefer, Epigenetics in Development. *Developmental Dynamics,* 236:1144-1156, 2007.
19. Ahmad Miremadi, Mikkel Z. Oestergaard, Paul D. P. Pharoah, and Carlos Caldas, Cancer genetics of epigenetic genes. *Human Molecular Genetics,* 2007, vol. 16, Review Issue 1, R28-R49.
20. Janet S. Graham, Stanely B. Kaye, and Robert Brown. The promises and pitfalls of epigenetic therapies in solid tumors. *European Journal of Cancer* 45 (2009), 1129-1136.
21. T. J. Walton, G. Li, R. Seth, S. E. McArdle, M. C. Bishop, and R. C. Rees, DNA demethylation and histone deacetylation inhibition co-operate to re-express estrogen receptor beta and induce apoptosis in prostate cancer cell-lines. *The Prostate* 68:210-222 (2008).
22. Oi Wah Stephanie Yap, Ganaphthy Bhat, Liang Liu, and Trygve O. Tollefsbol, Epigenetic modifications of the estrogen receptor beta gene in epithelial ovarian cancer cells. *Anticancer Research* 29:139-144 (2009).

What is claimed is:

1. A method of producing bee larvae that are at least 100% greater in weight than control larvae comprising feeding young worker bees a histone deacetylase (HDAC) inhibitor or a mixture of HDAC inhibitors and feeding bee larvae royal jelly secreted by these young worker bees, while the bee larvae of the control receive the royal jelly produced by young worker bees not fed with a HDAC inhibitor or a mixture HDAC inhibitors.

2. The method of claim 1, wherein the weight of the larvae feeding on the royal jelly produced by worker bees fed with the HDAC inhibitor or the mixture of HDAC inhibitors after 72 hrs increases higher than 1.5 times.

3. The method of claim 1, wherein the weight of the larvae feeding on the royal jelly produced by worker bees fed with the HDAC inhibitor or the mixture of HDAC inhibitors after 72 hrs increases by about 2 to 5 times.

4. The method of claim 1, wherein the weight of the larvae feeding on the royal jelly produced by worker bees fed with the HDAC inhibitor or the mixture of HDAC inhibitors after 72 hrs increases by about 3 to 5 times.

5. The method of claim 1, wherein the royal jelly has a changed ratio of 68 to 64 kDa protein of major royal jelly protein 3 (MRJP3).

6. The method of claim 5, wherein the ratio of 68 to 64 kDa protein of MRJP3 is changed by increasing about 1.5 to 12 times relative to a control.

7. The method of claim 6, wherein the ratio of 68 to 64 kDa protein of MRJP3 is changed by increasing about 4-12 times relative to a control.

8. The method of claim 7, wherein the ratio of 68 to 64 kDa protein of MRJP3 is changed by increasing about 2-10 times relative to a control.

9. The method of claim 8, wherein the ratio of 68 to 64 kDa protein of MRJP3 is changed by increasing about 2-6 times relative to a control.

10. The method of claim 9, wherein the ratio of 68 to 64 kDa protein of MRJP3 is changed by increasing about 2-4 times relative to a control.

11. The method of claim 9, wherein the ratio of 68 to 64 kDa protein of MRJP3 is changed by increasing about 1.5 to 5 times relative to a control.

12. The method of claim 1, wherein the bee larvae can be fed by worker bees on the royal jelly secreted therefrom or by human with the royal jelly collected from worker bees.

* * * * *